(12) United States Patent
Andrés-Gil et al.

(10) Patent No.: US 7,501,418 B2
(45) Date of Patent: Mar. 10, 2009

(54) FUSED HETEROCYCLIC ISOXAZOLINE DERIVATIVES AND THEIR USE AS ANTI-DEPRESSANTS

(75) Inventors: José Ignacio Andrés-Gil, Madrid (ES); Manuel Jesús Alcázar-Vaca, Toledo (ES); José Manuel Bartolomé -Nebreda, Toledo (ES); Francisco Javier Fernández-Gadea, Toledo (ES); Margaretha Henrica Maria Bakker, Alsbach-Haehnlein (DE); Antonius Adrianus Hendrikus Megens, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 377 days.

(21) Appl. No.: 10/524,123

(22) PCT Filed: Aug. 13, 2003

(86) PCT No.: PCT/EP03/50377

§ 371 (c)(1),
(2), (4) Date: Feb. 10, 2005

(87) PCT Pub. No.: WO2004/018483

PCT Pub. Date: Mar. 4, 2004

(65) Prior Publication Data

US 2006/0116378 A1    Jun. 1, 2006

(30) Foreign Application Priority Data

Aug. 15, 2002    (EP) .................................. 02078373

(51) Int. Cl.
| | | |
|---|---|---|
| A01N 43/54 | (2006.01) |
| A01N 43/40 | (2006.01) |
| A61K 31/445 | (2006.01) |
| A61K 31/497 | (2006.01) |
| C07D 211/32 | (2006.01) |
| C07D 211/68 | (2006.01) |
| C07D 211/80 | (2006.01) |
| C07D 213/02 | (2006.01) |
| C07D 261/20 | (2006.01) |
| C07D 239/00 | (2006.01) |
| C07D 237/26 | (2006.01) |
| C07D 237/36 | (2006.01) |
| C07D 413/00 | (2006.01) |
| C07D 417/00 | (2006.01) |
| C07D 419/00 | (2006.01) |
| C07D 471/00 | (2006.01) |
| C07D 487/00 | (2006.01) |
| C07D 491/00 | (2006.01) |
| C07D 495/00 | (2006.01) |
| C07D 497/00 | (2006.01) |

(52) U.S. Cl. ............................ 514/253.03; 514/254.02; 514/267; 514/318; 514/321; 514/322; 544/234; 544/250; 544/345; 544/368; 546/193; 546/198; 546/199

(58) Field of Classification Search ................. 514/318, 514/253.03, 267, 321, 322, 254.02; 544/368, 544/250, 234, 345; 546/193, 198, 199
See application file for complete search history.

(56) References Cited

U.S. PATENT DOCUMENTS 7,169,786 B2 *    1/2007    Andres-Gil et al. .... 514/253.03

FOREIGN PATENT DOCUMENTS

| EP | 0 361 577 B1 | 5/1993 |
| EP | 0 885 883 A1 | 12/1998 |
| WO | WO 95/07893 A1 | 3/1995 |
| WO | WO 97/25317 A1 | 7/1997 |
| WO | WO 99/67237 A1 | 12/1999 |
| WO | WO 02/066484 A1 | 8/2002 |

OTHER PUBLICATIONS

Cryan, J., et al., 5-HT1A and Beyond: The Role of Serotonin and its Receptors in Depression and the Antidepressant Response, Hum. Psychopharmacol. Clin. Exp. 15, 113-135 (2000).*
International Search Report for PCT/EP03/50377 dated Dec. 22, 2003.

* cited by examiner

*Primary Examiner*—James O Wilson
*Assistant Examiner*—Erich A Leeser
(74) *Attorney, Agent, or Firm*—Woodcock Washburn LLP

(57) ABSTRACT

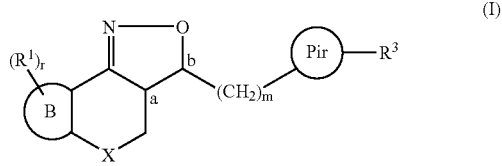

The invention concerns fused heterocyclic isoxazoline derivatives of Formula (I), the pharmaceutically acceptable acid or base addition salts thereof, the stereochemically isomeric forms thereof and the N-oxide form thereof, more in particular, tetrahydropyranoisoxazole, hexahydroisoxazolopyridine, tetrahydrothiopyrano isoxazole and hexahydrobenzoisoxazole derivatives fused to a heterocyclic ring system via the 6-membered ring of the bicyclic moiety as well as processes for their preparation, pharmaceutical compositions comprising them and their use as a medicine, in particular for treating depression, anxiety, movement disorders, psychosis, Parkinson's disease and body weight disorders including anorexia nervosa and bulimia, wherein the variables are defined as in Claim 1. The compounds have surprisingly been shown to have selective serotonine (5-HT) reuptake inhibitor activity as well as $\alpha_2$-adrenoceptor antagonist activity, compounds according to the invention are also suitable for treatment and/or prophylaxis in diseases where either one of the activities alone or the combination of said activities may be of therapeutic use.

7 Claims, No Drawings

FUSED HETEROCYCLIC ISOXAZOLINE DERIVATIVES AND THEIR USE AS ANTI-DEPRESSANTS

CROSS REFERENCE TO RELATED APPLICATIONS

This application is the national stage of Application No. PCT/EP03/50377, filed Aug. 13, 2003, which application claims priority from EP Patent Application No. 02078373.4 filed Aug. 15, 2002.

The invention concerns fused heterocyclic isoxazoline derivatives, more in particular tetrahydropyranoisoxazole, hexahydroisoxazolopyridine, tetrahydrothiopyrano-isoxazole and hexahydrobenzoisoxazole derivatives fused to a heterocyclic ring system via the 6-membered ring of the bicyclic moiety as well as processes for their preparation, pharmaceutical compositions comprising them and their use as a medicine, in particular for treating depression, anxiety, movement disorders, psychosis, Parkinson's disease and body weight disorders including anorexia nervosa and bulimia.

The invention also relates to novel combination of said fused heterocyclic isoxazoline derivatives with antidepressants, anxiolytics, antipsychotics and anti-Parkinson's disease drugs.

Tetrahydronaphtalene and indane derivatives showing anti-depressant activity are known from EP-361 577 B1. These compounds are typical monoamine reuptake blockers with additional $\alpha_2$-adrenoceptor antagonist activity and they show anti-depressant activity without being sedative.

The problems associated with the compounds according to the state of the art is that the compounds cause considerable side-effects, such as nausea, excitation, an increased heart rate and a reduced sexual function. Furthermore, it requires a long time, in particular 3-4 weeks, before the response starts.

The purpose of the present invention is to provide novel compounds for treating depression, anxiety, movement disorders, psychosis, schizophrenia and body weight disorders, in particular compounds that do not exhibit the aforementioned disadvantages.

The present invention relates to novel isoxazoline derivatives according to the general Formula (I)

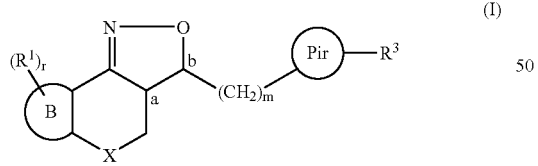

(I)

the pharmaceutically acceptable acid or base addition salts thereof, the stereochemically isomeric forms thereof and the N-oxide form thereof, wherein:

X is $CH_2$, N—$R^7$, S or O;

$R^7$ is selected from the group of hydrogen, alkyl, Ar, Ar-alkyl, alkylcarbonyl, alkyloxycarbonyl and mono- and dialkylaminocarbonyl;

B is a radical, optionally substituted with r radicals $R^1$, according to anyone of Formula (B-a) or (B-b) and fused to the isoxazolinyl moiety by either of the bond pairs (c,d), (d,e) or (e,f)

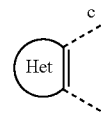

(B-a)

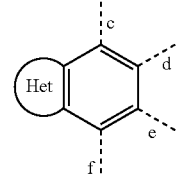

(B-b)

wherein

Het is an optionally substituted 5- or 6-membered heterocyclic ring, selected from the group of pyridinyl, pyrazinyl, pyrimidinyl, pyridazinyl, furanyl, thienyl, pyrrolyl, oxazolyl, thiazolyl, imidazolyl, pyrazolyl, isothiazolyl, isoxazolyl, oxadiazolyl and triazolyl;

each $R^1$ is, independently from each other, selected from the group of hydrogen, hydroxy, amino, nitro, cyano, halo and alkyl and, only when $R^1$ is attached to a N-atom, is further selected from the group of alkyloxyalkyl, alkyloxyalkyloxyaLkyl, alkyloxycarbonylalkyl, formyl, alkylcarbonyl, alkyloxycarbonyl, alkyloxyalkylcarbonyl and mono- and dialkylamino-carbonyl;

r is an integer ranging from 0 to 6;

a and b are asymmetric centers;

$(CH_2)_m$ is a straight hydrocarbon chain of m carbon atoms, m being an integer ranging from 1 to 4;

Pir is a radical according to any one of Formula (IIa), (IIb) or (IIc)

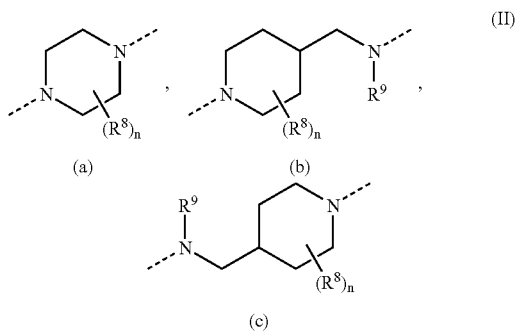

(II)

optionally substituted with n radicals $R^8$, wherein:

each $R^8$ is independently from each other, selected from the group of hydroxy, amino, nitro, cyano, halo and alkyl;

n is an integer ranging from 0 to 5;

$R^9$ is selected from the group of hydrogen, alkyl and formyl;

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S; and Ar is phenyl or naphthyl, optionally substituted with one or more halo, cyano, oxo, hydroxy, alkyl, formyl, alkyloxy or amino radicals.

More in particular, the invention relates to compounds according to Formula (I), the pharmaceutically acceptable acid or base addition salts thereof, the stereochemically isomeric forms thereof and the N-oxide form thereof, wherein $R^3$ is a radical according to any one of Formula (IIIa), (IIIb) or (IIIc)

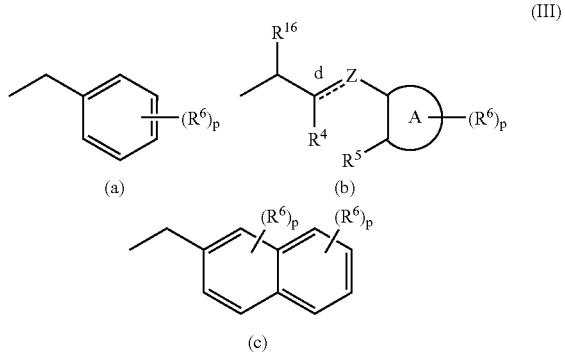

(III)

wherein:
d is a single bond while Z is a bivalent radical selected from the group of —CH$_2$—, —C(=O)—, —CH(OH)—, —C(=N—OH)—, —CH(alkyl)—, —O—, —S—, —S(=O)—, —NH— and —SH—; or d is a double bond while Z is a trivalent radical of formula =CH— or =C(alkyl)-;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group of hydrogen, alkyl, Ar, biphenyl, halo and cyano ; or $R^4$ and $R^5$ may be taken together to form a bivalent radical —$R^4$—$R^5$-selected from the group of —CH$_2$—, =CH—, —CH$_2$—CH$_2$—, —CH=CH—, —O—, —NH—, =N—, —S, —CH$_2$N(-alkyl)- , —N(-alkyl)CH$_2$—, —CH$_2$NH—, —NHCH$_2$—, —CH=N—, —N=CH, —CH$_2$O— and —OCH$_2$—;

each $R^6$ is independently from each other, selected from the group of hydroxy, amino, nitro, cyano, halo, carboxyl, alkyl, Ar, alkyloxy, Ar-oxy, alkyl-carbonyloxy, alkyloxycarbonyl, alkylthio, mono- and di(alkyl)amino, alkylcarbonylamino, mono- and di(aLkyl)aminocarbonyl, mono- and di(alkyl)aminocarbonyloxy, mono- and di(alkyl)aminoalkyloxy ; or two vicinal radicals $R^6$ may be taken together to form a bivalent radical —$R^6$—$R^6$ —selected from the group of —CH$_2$—CH$_2$—O—, —O—CH$_2$—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$— and $R^{16}$ is selected from the group of hydrogen, alkyl, Ar and Ar-alkyl.

Preferably, the invention relates to those compounds according to Formula (I), the pharmaceutically acceptable acid or base addition salts thereof, the stereochemically isomeric forms thereof and the N-oxide form thereof, wherein X=O; m=1; B is a radical according to Formula (B-a) or (B-b), Pir is a radical according to Formula (IIa) wherein n=0; $R^3$ is a radical according to according to any one of Formula (IIIa), (IIIb) or (IIIc) wherein d is a double bond while Z is a trivalent radical of formula =CH— or =C(alkyl)—; A is a phenyl ring ; $R^4$is hydrogen or alkyl ; $R^5$ and $R^{16}$ are each hydrogen ; $R^6$ is hydrogen or halo and p=1.

Preferably, the invention relates to those compounds according to Formula (I), the pharmaceutically acceptable acid or base addition salts thereof, the stereochemically isomeric forms thereof and the N-oxide form thereof, wherein Het is selected from the group of pyridinyl, thienyl and pyrrolyl, each radical optionally substituted on a N atom with a radical selected from the group of hydrogen, alkyl, alkyloxyallcyloxyalkyl, alkyloxycarbonylalkyl, alkylcarbonyl, alkyloxycarbonyl and alkyloxyalkylcarbonyl.

In the framework of this application, alkyl defines straight or branched saturated hydrocarbon radicals having from 1 to 6 carbon atoms, for example methyl, ethyl, propyl, butyl, 1-methylpropyl, 1,1-dimethylethyl, pentyl, hexyl ; or alkyl defines cyclic saturated hydrocarbon radicals having from 3 to 6 carbon atoms, for example cyclopropyl, methylcyclopropyl, cyclobutyl, cyclopentyl and cyclohexyl. The definition of alkyl also comprises alkyl radicals that are substituted with one or more halo, cyano, oxo, hydroxy, formyl or amino radicals, for example hydroxyalkyl, in particular hydroxymethyl and hydroxyethyl and polyhaloalkyl, in particular difluoromethyl and trifluoromethyl.

In the framework of this application, Ar is phenyl or naphthyl, optionally substituted with one or more halo, cyano, oxo, hydroxy, alkyl, formyl, alkyloxy or amino radicals, such as for example, 3-fluoro-phenyl of 3-fluoro-naphthyl.

In the framework of this application, halo is generic to fluoro, chloro, bromo and iodo.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid ; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperazinyl radical are N-oxidized.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure, respectively denoted a and b in Formula (I). Due to the synthetic pathway followed for the synthesis of the tricyclic system, the configuration of those two asymmetric centers a and b is predetermined, so that the relative configuration of center a is S* and of center b is R*.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", Drug Delivery Systems, 1985, pp. 112-176, and Drugs, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

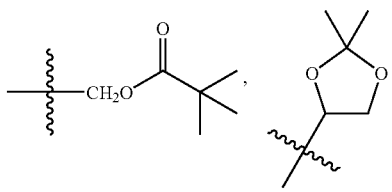

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such, as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds according to the invention, in particular compounds according to Formula (I), the pharmaceutically acceptable acid or base addition salts thereof, the stereochemically isomeric forms thereof and the N-oxide form thereof, have surprisingly been shown to have selective serotonine (5-HT) reuptake inhibitor activity in combination with additional α$_2$-adrenoceptor antagonist activity and show a strong anti-depressant and/or anxiolytic activity and/or antipsychotic and/or a body weight control activity without being sedative. Also, in view of their selective serotonine (5-HT) reuptake inhibitor as well as α$_2$-adrenoceptor antagonist activity, compounds according to the invention are also suitable for treatment and/or prophylaxis in diseases where either one of the activities alone or the combination of said activities may be of therapeutic use. In particular, the compounds according to the invention may be suitable for treatment and/or prophylaxis in the following diseases:

Central nervous system disorders, including:

Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder, recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.

Anxiety disorders, including panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder and anxiety disorder not otherwise specified.

Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.

Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III.

Cognitive disorders due to cognitive impairment resulting from other medical conditions.

Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.

Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.

Akinesia, akinetic-rigid syndromes, dyskinesia and medication-induced parkinsonism, Gilles de la Tourette syndrome and its symptoms, tremor, chorea, myoclonus, tics and dystonia.

Attention-deficit/hyperactivity disorder (ADHD).

Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.

Dementia of the Alzheimer's type, with early or late onset, with depressed mood.

Behavioral disturbances and conduct disorders in dementia and the mentally retarded, including restlessness and agitation.

Extra-pyramidal movement disorders.

Down's syndrome.

Akathisia.

Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.

AIDS-associated dementia.

Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain, tic douloureux and atypical face pain, nerve root damage and arachnoiditis, geriatric pain, central pain and inflammatory pain. Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.

Addiction disorders, including:

Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/or other substances, particularly useful for treating withdrawal from the above substances and alcohol withdrawal delirium.

Mood disorders induced particularly by alcohol, amphetamines, caffeine, cannabis, cocaine, hallucinogens, inhalants, nicotine, opioids, phencyclidine, sedatives, hypnotics, anxiolitics and other substances.

Anxiety disorders induced particularly by alcohol, amphetamines, caffeine, cannabis, cocaine, hallucinogens, inhalants, nicotine, opioids, phencyclidine, sedatives, hypnotics, anxiolitics and other substances and adjustment disorders with anxiety.

Smoking cessation.

Body weight control, including obesity.

Sleep disorders and disturbances, including

Dyssomnias and/or parasomnias as primary sleep disorders, sleep disorders related to another mental disorder, sleep disorder due to a general medical condition and substance-induced sleep disorder.

Circadian rhythms disorders.

Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The present invention thus also relates to compounds according to Formula (I), the pharmaceutically acceptable acid or base addition salts thereof, the stereochemically isomeric forms thereof, the N-oxide form thereof, as well as the prodrugs thereof for use as a medicine, in particular for the treatment and/or prophylaxis of depression, anxiety, movement disorders, psychosis, Parkinson's disease and body weight disorders.

The present invention also relates to a method for the treatment and/or prophylaxis of diseases where either one of the activities (selective serotonine (5-HT) reuptake inhibitor and $\alpha_2$-adrenoceptor antagonist activity) alone or the combination of said activities may be of therapeutic use, in particular for the treatment and/or prophylaxis of depression, anxiety, movement disorders, psychosis, Parkinson's disease and body weight disorders comprising administering to a human in need of such administration an affective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof and the N-oxide form thereof or a prodrug as defined above.

The compounds according to the invention, in particular the compounds according to Formula (I), the pharmaceutically acceptable acid or base addition salts thereof, the stereochemically isomeric forms thereof and the N-oxide form thereof and the prodrugs, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds according to the invention may also be suitable as add-on treatment and/or prophylaxis in the above listed diseases in combination with any combination of compounds selected from the group of antidepressants, anxiolytics, antipsychotics and/or anti-Parkinson's disease drugs which are currently available or in development or which will become available in the future, to improve efficacy and/or onset of action. This is evaluated in rodent models in which antidepressants, anxiolytics, antipsychotics and/or anti-Parkinson's disease drugs are shown to be active. For example, compounds are evaluated in combination with antidepressants, anxiolytics, antipsychotics and/or anti-Parkinson's disease drugs for attenuation of stress-induced hyperthermia.

The invention therefore also relates to a pharmaceutical composition comprising the compounds according to the invention, in particular the compounds according to Formula (I), the pharmaceutically acceptable acid or base addition salts thereof, the stereochemically isomeric forms thereof and the N-oxide form thereof, and the prodrugs and one or more other compounds selected from the group of antidepressants, anxiolytics, antipsychotics and anti-Parkinson's disease drugs.

The invention also relates to the use of a pharmaceutical composition according to the invention for the manufacture of a medicament to improve efficacy and/or onset of action in the treatment and/or prophylaxis of depression, anxiety, movement disorders, psychosis, Parkinson's disease and body weight disorders.

Further, the invention relates to the use of a compound according to the invention for the manufacture of a medicament for the treatment and/or prophylaxis of depression, anxiety, movement disorders, psychosis, Parkinson's disease and body weight disorders, said treatment comprising the simultaneous or sequential administration of a compound according to the invention and one or more other compounds selected from the group of antidepressants, anxiolytics, antipsychosis and anti-Parkinson's drugs. The invention further relates to a process for making a pharmaceutical composition comprising mixing a compound according to the invention, in particular the compounds according to Formula (I), the pharmaceutically acceptable acid or base addition salts thereof, the stereochemically isomeric forms thereof and the N-oxide form thereof, and the prodrugs, or any subgroup thereof and a compound selected from the group of antidepressants, anxiolytics, antipsychotics and anti-Parkinson's disease drugs and a pharmaceutically acceptable carrier.

In vitro receptor and neurotransmitter transporter binding and signal-transduction studies can be used to evaluate the α₂-adrenoceptor antagonism activity and serotonine (5-HT reuptake inhibitor activity of the present compounds. As indices for central penetration and potency to block the α₂-adrenoceptors and serotonin transporters, respectively, ex vivo α₂-adrenoceptor and serotonin transporter occupancy can be used. As indices of α₂-adrenoceptor antagonism in vivo, the reversal of the loss of righting reflex, observed in rats after subcutaneous injection or oral dosage of the compound before intravenous medetomidine administration in rats can be used (medetomidine-test). As indices of serotonine (5-HT) reuptake inhibition activity, the inhibition of head-twitches and excitation in rats, observed after subcutaneous injection or oral dosage of the compound before subcutaneous p-chloroamphetamine administration in rats can be used (pCA-test).

The compounds according to the invention can generally be prepared by a succession of steps, each of which is known to the skilled person.

In particular, the compounds according to Formula (I) with a Pir-radical according to Formula (IIa), (IIb) or (IIc) can be prepared by a nucleophilic substitution reaction with a substituted piperazine according to Formula (V) on an intermediate compound of Formula (IV). These reactions may be carried out in a reaction inert solvent such as 1,4-dioxane, methylisobutylketone (MIBK), acetonitrile or N,N'-dimethylformamide, in the presence of a suitable base such as NaHCO₃, Na₂CO₃, piperidine or triethylamine, or even without a base, using in this latter case excess of reagent of Formula (V). Convenient reaction temperatures range between 100° C. and 150° C.

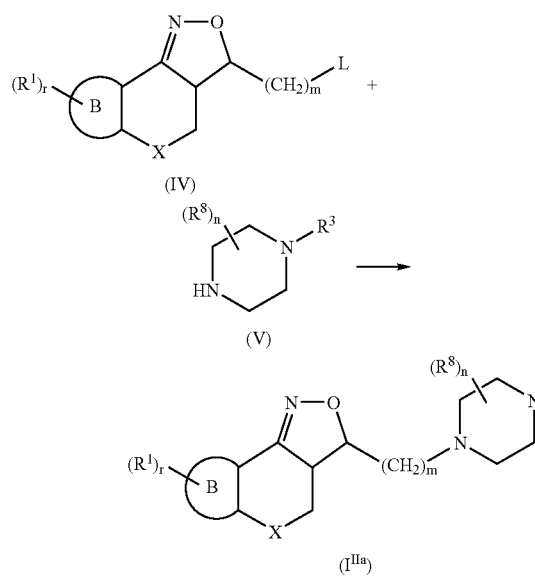

In compound (IV), L represents any suitable reactive leaving group, in particular halo, such as chloro, bromo or iodo or sulfonyloxy, such as 4-methylsulphonyloxy or 4-methylbenzenesulfonyloxy.

The compounds according to the invention can easily be converted into each other. In case the B-radical is an N-containing heterocyclic radical, such as e.g. indol, the nitrogen atom of such a final compound according to Formula (I') can be alkylated or acylated according to art-known procedures to give final compounds of Formula (I''). Alkylation reactions can be carried out in the presence of the corresponding alkylating agent, for example any haloalkyl compound, in the presence of a base, such as NaOH, KOH, Na₂CO₃, K₂CO₃ or a mixture thereof, and an inert solvent, for example acetonitrile, tetrahydrofuran or a mixture thereof. Acylation reactions can be carried out in the presence of an acylating agent, for example acylhalides, isocyanates or acid anhydrides ; a strong base, such as NaOH, KOH or BEMP (2-tert-butyl-imino-2-diethylamino-1,3-dimethylperhydro-1,3,2-diazphosphorine) either or not supported in an inert polymer, such as polystyrene; and an inert solvent, for example dichloromethane or tetrahydrofuran. L is a leaving group, in particular halo such as chloro, bromo, iodo; or sulphonyloxy or 4-methylsulphonyloxy ; and $R^1$ is any alkyl or acyl group.

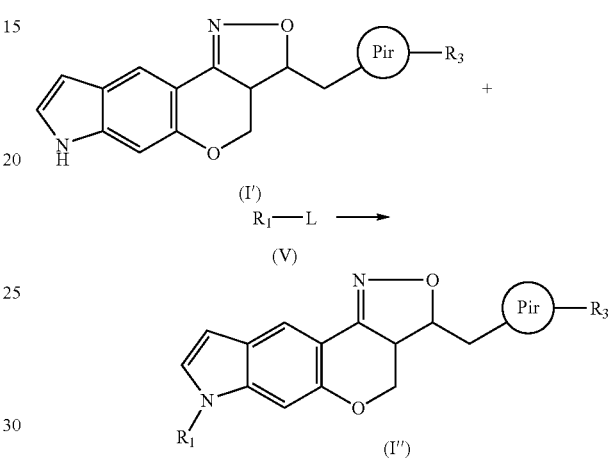

The starting materials and some of the intermediate compounds are compounds that are either commercially available or may be prepared according to conventional reaction procedures generally known in the art. For example, intermediate compounds of Formula (IV') in which X=O may be prepared according to the following reaction scheme 1.

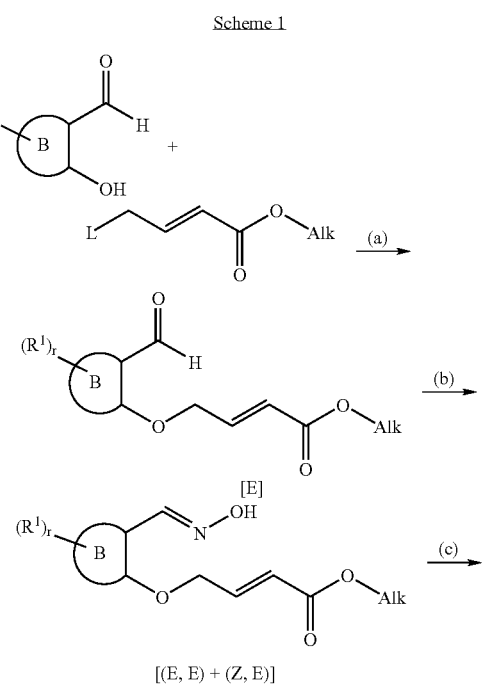

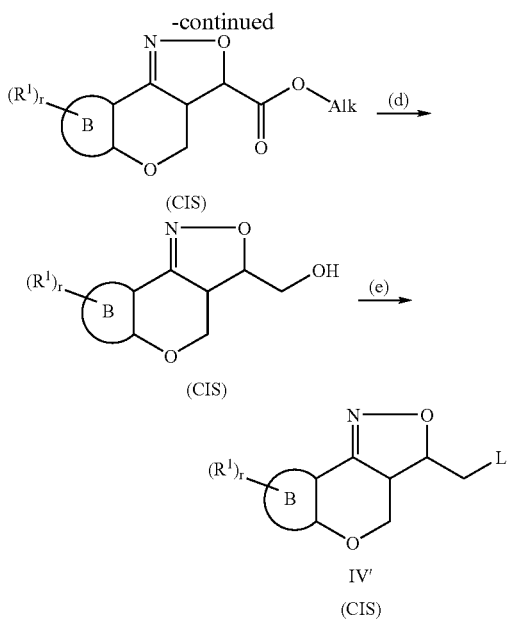

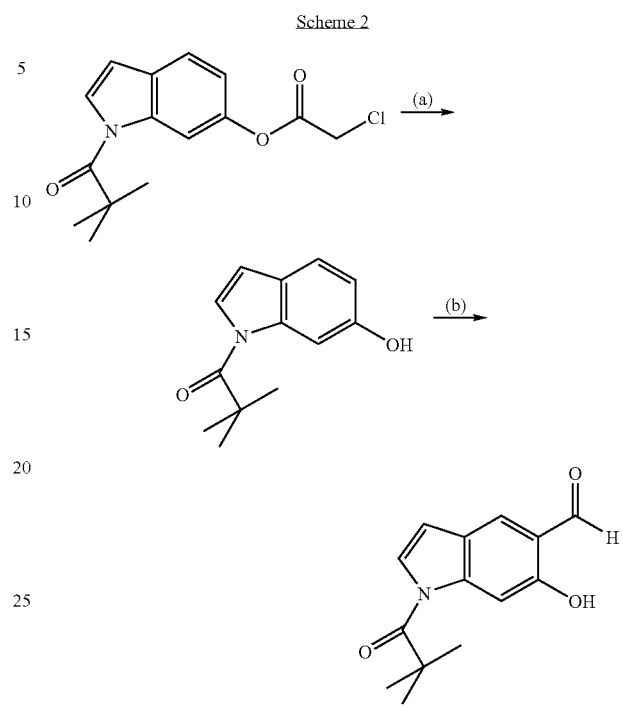

An intermediate compound of Formula (IV') can be prepared from hydroxyaldehydes by reaction with commercially available crotonates in the presence of a base, such as $K_2CO_3$, $Na_2CO_3$ or NaH in an inert solvent, such as 2-propanone or dimethylformamide (step a). The resulting intermediate compound is converted into the oxime in a temperature range of −10° C. to 0° C. using art-known techniques, such as hydroxylamine hydrochloride in the presence of a suitable base, such as AcONa, $NaHCO_3$ or pyridine in a reaction inert solvent, for example ethanol (step b). The resulting oxime-intermediate compound is further oxidized into its nitrile oxide and the subsequent in situ intramolecular cycloaddition yields an isoxazoline compound (step c). The oxidation can be carried out using sodium hypochlorite solution in the presence of triethylamine in an inert solvent, such dichloromethane at room temperature. Oxidation can also be performed using chloramine-T hydrate (N-chloro4-methylbenzene-sulphonamide, sodium salt), by stirring and heating in a solvent such as refluxing ethanol. At this stage two steroisomers are formed. Reduction of the carbonyl radical in the presence of a suitable reducing agent, for example sodium borohydride, in a suitable solvent, such as water, alcohol, tetrahydrofuran or a mixture thereof, generally at room temperature yields the hydroxy-intermediate compound (step d), which is further converted into intermediate compound (IV') using standard techniques (step e). For example, reaction with methanesulfonylchloride or 4-methylbenzenesulfonyl-chloride in the presence of a base, such as triethylamine, in a reaction inert solvent, for example dichloromethane, at reaction temperatures ranging between 0° C. and room temperature yields the corresponding sulfonyloxy derivative intermediate compound (IV'). The corresponding halo-derivative can also be prepared, e.g. by treating the hydroxy-intermediate compound with triphenylphosphine, in the presence of tetrachloromethane, in a reaction inert solvent, such as tetrahydrofuran, and by stirring and refluxing the mixture. In some cases a protecting group (for example a tert-butoxycarbonyl group) may be removed in step (d).

Specifically, indol-fused isoxazolidine derivatives may also be prepared as in the following reaction scheme 2 in which the hydroxyaldehyde intermediate compound is prepared as describe by Katsunori Teranishi et al. in *Synthesis*, 1994, (10), 1018-1020 by hydrolysis of the ester in the presence of a strong base, such as LiOH or NaOH, water and an inert solvent, for example 1,4-dioxane or tetrahydrofuran. The resulting hydroxy intermediate compound is formylated using art-known procedures to yield the hydroxyaldehyde intermediate compound, such as a reaction with paraformaldehyde in the presence of an appropriate salt, for example $MgCl_2$, a base, for example triethylamine or diisopropylethylamine, and in an inert solvent, for example acetonitrile or tetrahydrofuran.

Specifically, pyrazine-fused isoxazolidine derivatives may be prepared according to the following reaction scheme 3.

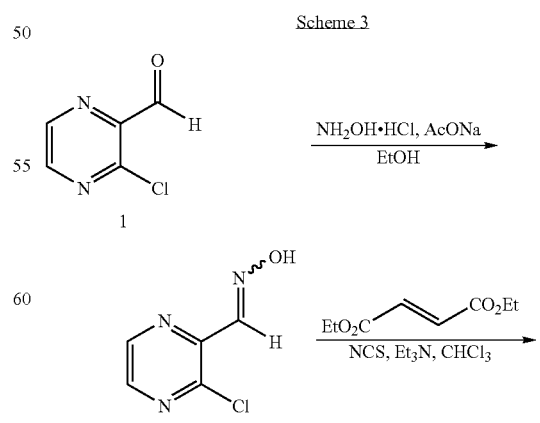

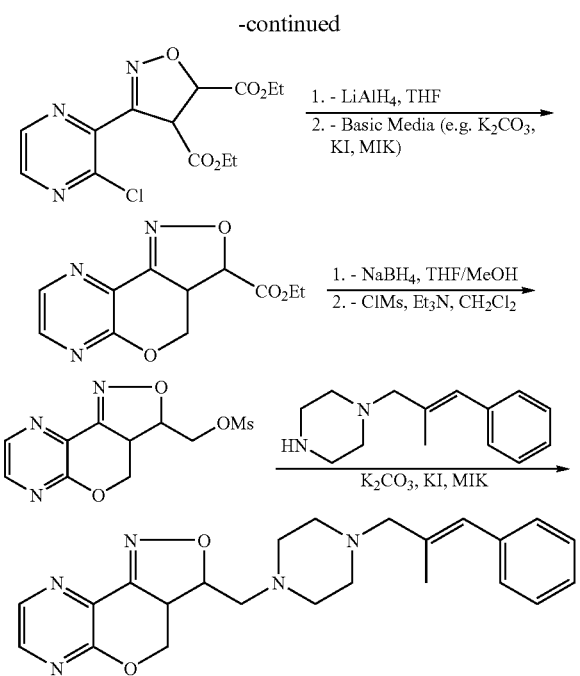

[1] Described in Turck, A.; Mojovic, L.; Queguiner, G. Synthesis, 11, 1988, 881-884

Specifically, pyridazine-fused isoxazolidine derivatives may be prepared according to either one of the following schemes 4 and 5.

Scheme 4

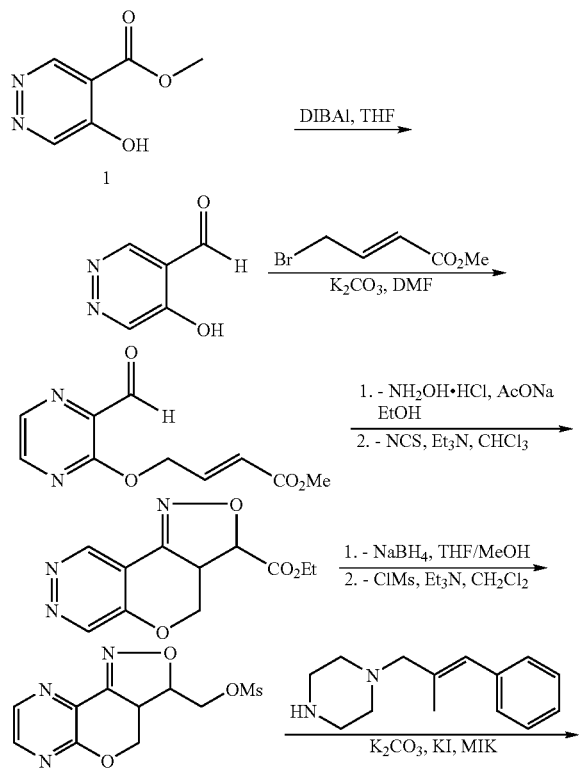

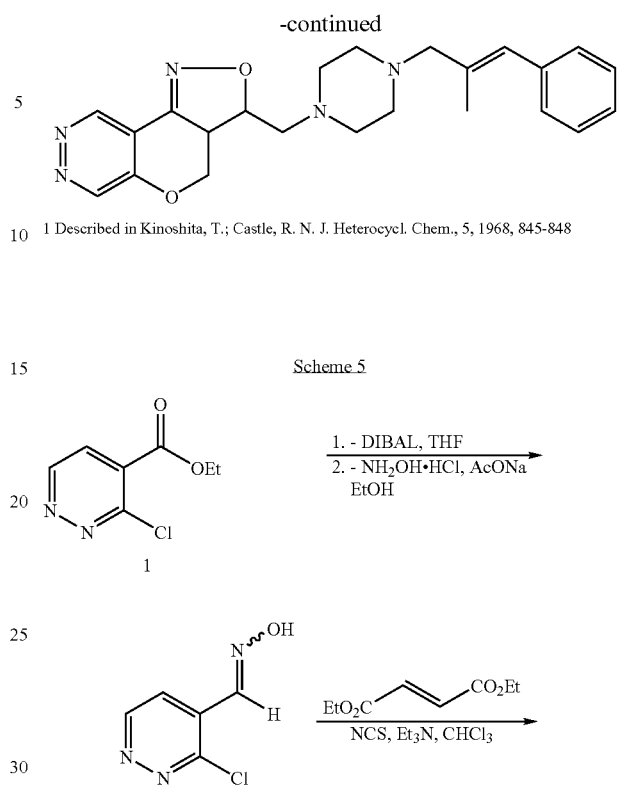

[1] Described in Kinoshita, T.; Castle, R. N. J. Heterocycl. Chem., 5, 1968, 845-848

Scheme 5

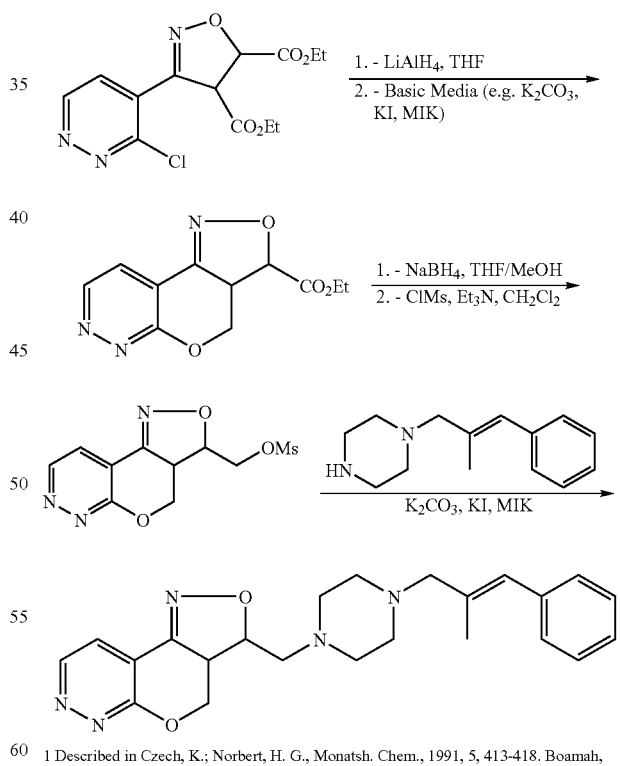

[1] Described in Czech, K.; Norbert, H. G., Monatsh. Chem., 1991, 5, 413-418. Boamah, P. Y.; Haider, N.; Heinisch, G. Arch. Pharm., 1990, 323-324. Giani, R. P.; Malandrino, S.; Tonon, G.; EP 230402 A2

Specifically, pyrimidine-fused isoxazolidine derivatives may be prepared according to either one of the following schemes 6 and 7.

Scheme 6
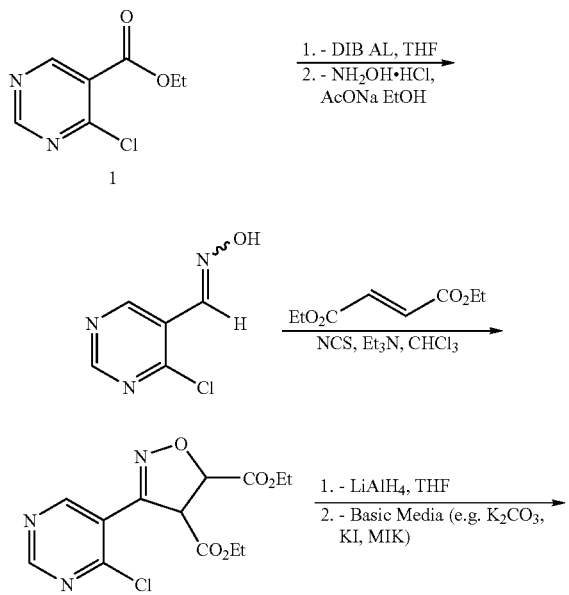
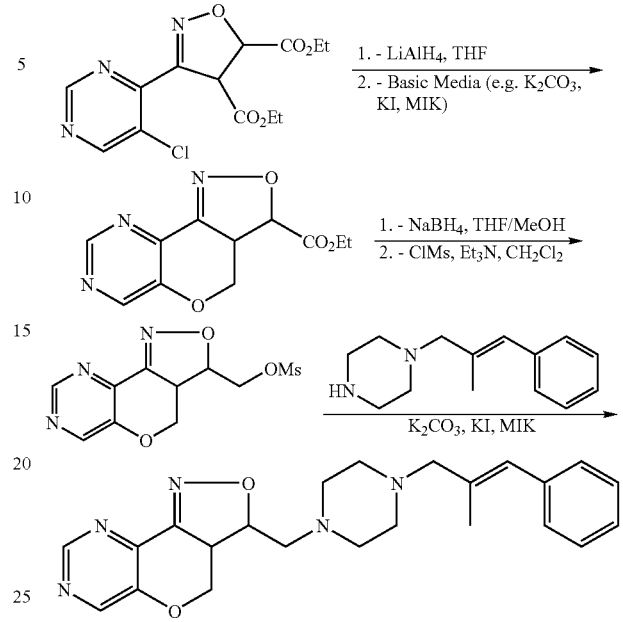
Scheme 7
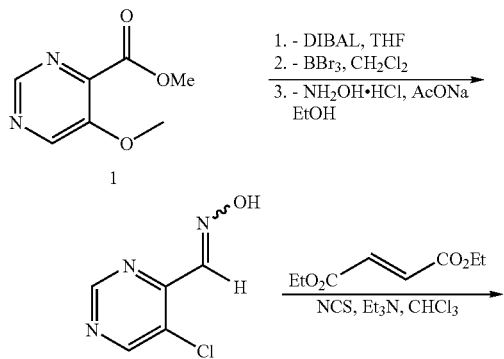
Specifically, benzofuran-fused isoxazolidine derivatives may be prepared according to the following scheme 8.
Scheme 8
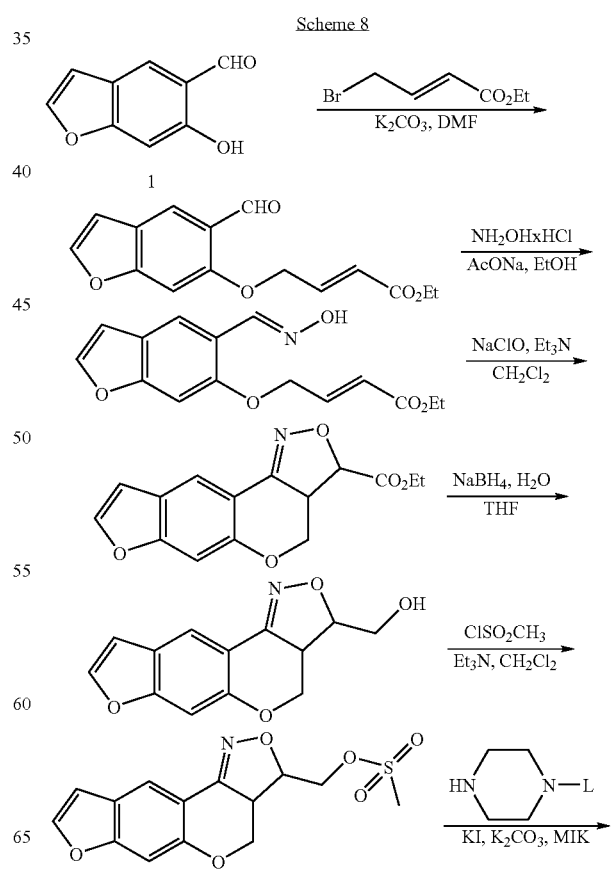

-continued

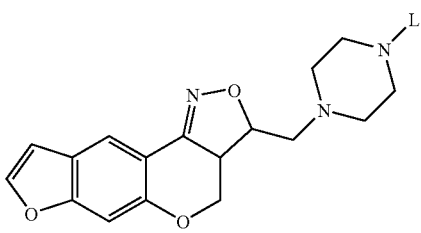

1 Described by Worden, Leonard R.; Kaufman, Kurt Dunn; Weis, James A.; Schaaf, Thomas K. in J. Org. Chem. (1969), 34(8), 2311-13.

Specifically, benzoxazole-fused isoxazolidine derivatives may be prepared according to the following scheme 9.

Scheme 9

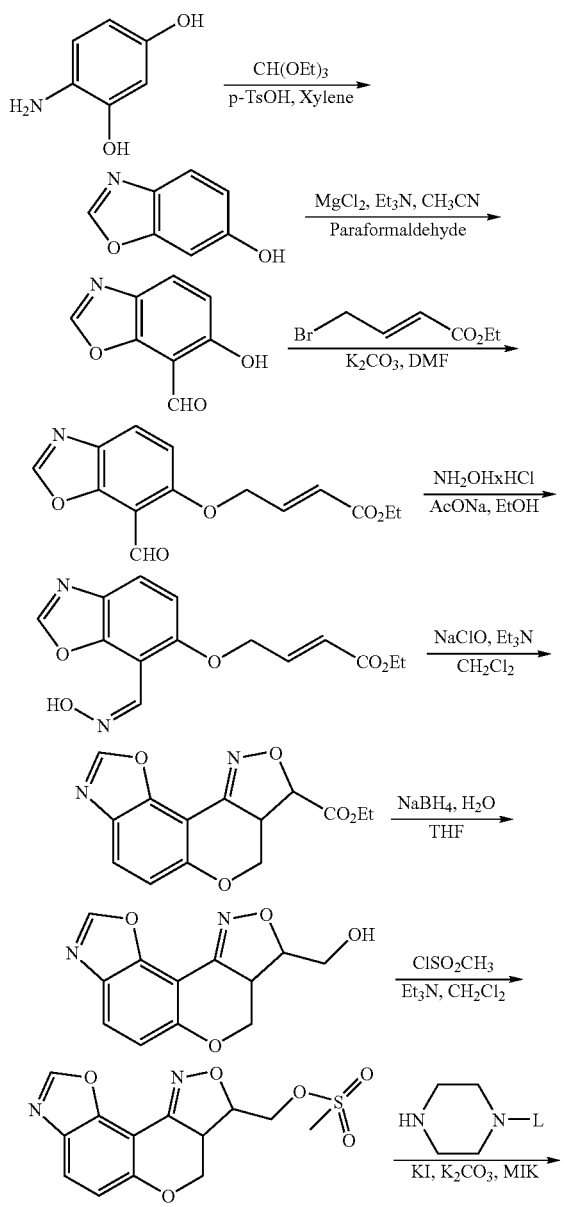

-continued

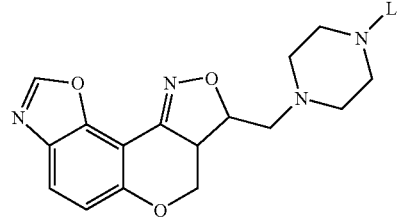

The following examples illustrate the present invention without being limited thereto.

Experimental Part

The carbon ring numbering system for the compounds according to Formula (I-B-b) used in this application is as follows:

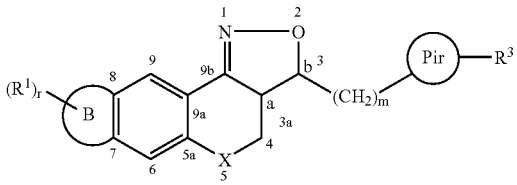

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The stereogenic centers a and b in Formula (I) have respectively the ring numbers 3a and 3.

Hereinafter, "DMF" is defined as N,N-dimethylformamide, "DIPE" is defined as diisopropyl ether, "ACN" is defined as acetonitrile, "DCM" is defined as dichloromethane and "THF" is defined as tetrahydrofurane.

A. Preparation of the Intermediate Compounds

Example A.1

Preparation of Intermediate Compound 7

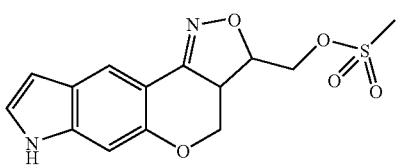

a) To a solution of 57.1 g (0.176 mol) of chloro-acetic acid 1-(2,2-dimethyl-propionyl)-1H-indol-6-yl ester in 500 ml of 1,4-dioxane, a solution of 5.05 g (0.211 mol) of LiOH in 100 ml of water was added portionwise at room temperature. The reaction was stirred for 1 h at room temperature. Then DCM and a 2N solution of HCl in water were added. The organic layer was separated, dried (Na$_2$SO$_4$), filtered off and the solvent evaporated. The residue was purified by short open column chromatography over silica gel (eluents: DCM and DCM/Ethyl acetate 95/5). The desired fractions were collected and the solvent evaporated. Yielding: 28.3 g (74%) of 1-(6-Hydroxy-indol-1-yl)-2,2-dimethyl-propan-1-one (intermediate compound 1).

b) To a mixture of intermediate compound 1 (24.13 g, 0.111 mol), magnesium chloride (15.9 g, 0.167 mol) and diisopropylethylamine (72.5 ml, 0.416 mol) in 600 ml of acetonitrile, 13.4 g (0.443 mol) of paraformaldehyde were added. The reaction was heated to reflux for 60 min, then additional 13.3 g (0.443 mol) of paraformadehyde were added. The reaction was heated to reflux for 60 min and 13.3 g (0.443 mol) of paraformaldehyde were added again. The reaction was heated to reflux for 2 h. The reaction was allowed to reach room temperature. Then a 1N solution of HCl in water and DCM were added. The organic layer was separated, dried ($Na_2SO_4$), filtered off and the solvent evaporated. The residue was purified by short open column chromatography over silica gel (eluent: DCM). The desired fractions were collected and the solvent evaporated. Yielding: 12.83 g (47%) of 1-(2,2-Dimethyl-propionyl)-6-hydroxy-1H-indole-5-carbaldehyde (intermediate compound 2).

c) 4-bromo-2-butenoic acid ethyl ester 14.2 ml (0.082 mol) was added portionwise to a mixture of intermediate compound 2 (13.6 g, 0.055 mol) and $K_2CO_3$ (13.68 g, 0.099 mol) in DMF (60 ml). The reaction mixture was stirred for 6 hours at room temperature, filtered and the filtrate was evaporated to dryness. The residue was washed with water, then extracted with DCM. The separated organic layer was dried ($Na_2SO_4$), filtered, and the solvent was evaporated. The residue was purified by short open column chromatography over silica gel (eluent: DCM and DCM/Ethyl acetate 9/1). The desired fractions were collected and the solvent evaporated. Yielding: 21.05 g (100%, crude yield) of 4-[1-(2,2-Dimethyl-propionyl)-5-formyl-1H-indol-6-yloxy]-but-2-enoic acid ethyl ester (intermediate compound 3).

d) Hydroxylamine hydrochloride (4.59 g, 0.066 mol) was added to a mixture of intermediate compound 3 (21.05 g, 0.055 mol) and sodium acetate (6.8 g, 0.066 mol) in ethanol (250 ml). The reaction mixture was stirred for 1 h at 0° C., then water was added and extracted with DCM. The separated organic layer was dried ($Na_2SO_4$), filtered, and the solvent was evaporated. Yielding: 21.0 g (100%, crude yield) of 4-[1-(2,2-Dimethyl-propionyl)-5-(hydroxyimino-methyl)-1H-indol-6-yloxy]-but-2-enoic acid ethyl ester (intermediate compound 4).

e) NaClO, 4% (176.4 ml, 0.140 mol) was added portionwise at 0° C. to a solution of intermediate compound 4 (19.4 g, 0.052 mol) in DCM (200 ml). The reaction was stirred for 1 h at room temperature. Then $Et_3N$ (10.9 ml, 0.078 mol) was added dropwise at 0° C. The reaction mixture was stirred for 3 hours at room temperature, then organic layer was separated, dried ($Na_2SO_4$), filtered, and the filtrate was evaporated. The residue was purified by short open column chromatography over silica gel (eluent: DCM and DCM/Ethyl acetate 95/5). The desired fractions were collected and the solvent was evaporated. The residue was washed with diisopropyl ether and collected. Yielding: 4.25 g (22%) of 7-(2,2-Dimethyl-propionyl)-3a,4-dihydro-3H,7H-2,5-dioxa-1,7-diaza-dicyclopenta[a,g]naphthalene-2-carboxylic acid ethyl ester (intermediate compound 5).

f) $NaBH_4$ (1.23 g, 0.0325 mol) was added portionwise to a solution of intermediate compoundn 5 (4.25 g, 0.013 mol) in THF (100 ml) and $H_2O$ (10 ml), stirred and cooled on an ice-bath. The resulting reaction mixture was stirred for 4 hours at room temperature. The reaction mixture was treated with a 10% aqueous solution of ammonium chloride and extracted with DCM. The separated organic layer was dried ($Na_2SO_4$), filtered and the solvent evaporated. Yielding: 3.03 g of (3a,4-dihydro-3H,7H-2,5-dioxa-1,7-diaza-dicyclopenta[a,g]naphthalen-3-methanol (intermediate compound 6).

g) $Et_3N$ (1.4 ml, 0.0101 mol) was added to a solution of intermediate compound 6 (1.65 g, 0.00675 mol) in DMF (15 ml). The mixture was cooled in an ice-bath. Methanesulfonyl chloride (0.58 ml, 0.0075 mol) was added and the resulting reaction mixture was stirred for 1 h at room temperature. Then, a saturated aqueous solution of $NaHCO_3$ was added and the mixture was extracted with DCM, dried ($Na_2SO_4$), filtered and the solvent was evaporated. The residue was washed with diisopropyl ether and the solid was collected. Yielding: 1.99 g (91%) of methanesulfonic acid 3a,4-dihydro-3H,7H-2,5-dioxa-1,7-diaza-dicyclopenta[a,g]naphthalen-3-ylmethyl ester (intermediate compound 7).

Example A.2

Preparation of Intermediate Compound 15

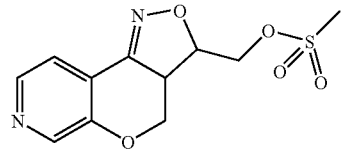

a) To a mixture of NaH (22.5 g, 0.6 mol) in 50 ml of THF a solution of 3-hydroxypyridine in 500 ml of THF was added dropwise at 0° C. under nitrogen atmosphere. The reaction was stirred for 15 min at 0° C., the a solution of methoxymethylchloride (45 ml, 0.55 mol) in 200 ml of THF was added portionwise at 0° C. The reaction was stirred at room temperature overnight, then quenched with a 10% aqueous solution of ammonium chloride and extracted with ethyl acetate, dried ($Na_2SO_4$), filtered and the solvent was evaporated. The residue was purified by short open column chromatography over silica gel (eluent: Heptane/Ethyl acetate 3/1 and 2/1). The desired fraction was collected and the solvent evaporated. Yielding: 38.15 g (55%) of 3-methoxymethoxy-pyridine (intermediate compound 8).

b) To a solution of intermediate compound 8 (19 g, 0.14 mol) and tetramethylethylene-diamine (23.2 ml, 0.15 mol) in 500 ml of ethyl ether, 60 ml of a solution 2.5M of butyllithium in THF was added dropwise at −78° C. under nitrogen atmosphere. The reaction was stirred for 2 h at −78° C., then methyl formate (10.9 ml, 0.18 mol) was added dropwise at −78° C. The mixture was allowed to reach room temperature and was stirred at this temperature overnight. Then a 10% aqueous solution of citric acid was added and the organic layer was separated, dried ($Na_2SO_4$), filtered and the solvent was evaporated. The residue was purified by short open column chromatography over silica gel (eluent: Heptane/Ethyl acetate 2/1). The desired fractions were collected and the solvent evaporated. Yielding: 18.5 g (80%) of 3-methoxymethoxypyridine-4-carboxaldehyde (intermediate compound 9).

c) Hydroxylamine hydrochloride (17.22 gg, 0.248 mol) was added at 0° C. to a mixture of intermediate compound 9 (34.08 g, 0.208 mol) and sodium acetate (25.59 g, 0.312 mol) in ethanol (250 ml). The reaction mixture was stirred overnight at room temperature, then water was added and extracted with DCM. The separated organic layer was dried ($Na_2SO_4$), filtered, and the solvent was evaporated. The residue was washed with diisopropylether with few drops of DCM and the solid was collected. Yielding: 26.24 g (69%) of 3-methoxymethoxy-pyridine-4-carbaldehyde oxime (intermediate compound 10).

d) To a mixture of intermediate compound 10 (26.24 g, 0.143 mol) in 400 ml of DCM, NaClO (4%) (485 ml, 0.286 mol) was added dropwise at 0° C. The reaction was stirred for 1 h at 0° C. and 2 h at room temperature. Then dimethyl fumarate (31.0 g, 0.215 mol) was added at 0° C. and triethylamine (29.6 ml, 0.215 mol) was added dropwise at 0° C. The reaction was stirred overnight at room temperature. The organic layer was separated, dried ($Na_2SO_4$), filtered and the solvent was evaporated. The residue was purified by short open column chromatography over silica gel (eluent: Heptane/Ethyl acetate 1/1, 1/3 and pure ethyl acetate). The desired fractions were collected and the solvent evaporated. Yielding: 13.45 g (29%) of 3-(3-methoxymethoxy-pyridin-4-yl)-4,5-dihydro-isoxazole-4,5-dicarboxylic acid dimethyl ester (intermediate compound 11).

e) To a solution of 13.45 g (0.041 mol) of intermediate compound 11, 52.1 ml of a solution 1M of lithiumaluminium hydride was added dropwise at 0° C. under nitrogen atmosphere. The reaction was stirred for 2 h at 0° C. The excess of hydride was quenched with a saturated aqueous solution of ammonium chloride. The solid was filtered off through a CELITE pad and the filtrate was extracted with ethyl acetate. The organic layer was separated, dried ($Na_2SO_4$), filtered and the solvent was evaporated. The residue was purified by short open column chromatography over silica gel (eluent: Ethyl acetate, Ethyl acetate/MeOH saturated with ammonia 97.5/2.5, 95/5 and 9/1). The desired fractions were collected and the solvent evaporated. Yielding: 3.8 g (34%) of [4-hydroxymethyl-3-(3-methoxymethoxy-pyridin-4-yl)-4,5-dihydro-isoxazol-5-yl]-methanol (intermediate compound 12).

f) To a solution of intermediate compound 12 (3.8 g, 0.0142 mol) in 100 ml of DCM, 25 ml of triflouroacetic acid were added portionwise at room temperature. The reaction was stirred overnight at room temperature. The solvent was evaporated and the residue was co-evaporated with ethanol. Yielding 4.79 g (100, crude product) of 4-(4,5-bis-hydroxymethyl-4,5-dihydro-isoxazol-3-yl)-pyridin-3-ol (intermediate compound 13).

g) To a solution of intermediate compound 13 (4.8 g, 0.0142 mol) in 50 ml of THF, triethylamine (19.9 ml, 0.0142 mol) at room temperature. The mixture was stirred at room temperature for 15 min, then triphenyl phosphine polymer bounded (loading 1.6 mmol/g) was added (17.75 g, 0.0284 mol) at room temperature and diethylazadicarboxylate (27.8 ml, 0.0178 mol) was added dropwise at room temperature. The reaction was heated to reflux for 2 h. The solid was filtered off through a CELITE pad and the filtrate was evaporated. The residue was dissolved in DCM and treated with water. The organic layer was separated, dried ($Na_2SO_4$), filtered and the solvent was evaporated. The residue was washed with acetonitrile/diisopropyl ether and the solid was collected. Yielding 3.07 g (100%, crude product) of (3a,4-dihydro-3H-2,5-dioxa-1,7-diaza-cyclopenta[a]naphthalen-3-yl)-methanol (intermediate compound 14).

h) Intermediate compound 14 (1.72 g, 0.0083 mol) was treated under the reaction conditions described in Example A.1 g using DCM as solvent. Yielding: 0.66 g of methanesulfonic acid 3a,4-dihydro-3H-2,5-dioxa-1,7-diaza-cyclopenta[a]naphthalen-3-ylmethyl ester (intermediate compound 15).

Example A.3

Preparation of Intermediate Compound 16

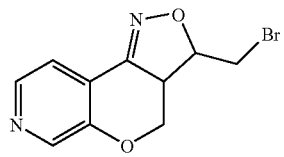

To a solution of intermediate compound 14 (1 g, 0.0048 mol) and $CBr_4$ (2.41 g, 0.0073 mol) in 100 ml of DCM, triphenyl phosphine polymer bounded (loading 1.6 mmol/g) was added (4.56 g, 0.0073 mol). The reaction was stirred overnight at room temperature, then the solid was filtered off through a CELITE pad and the filtrate was evaporated. The residue was purified by short open column chromatography over silica gel (eluent: DCM/Ethyl acetate 1/1). The desired fractions were collected and the solvent evaporated. Yielding: 0.62 g (48%) of 3-bromomethyl-3a,4-dihydro-3H-2,5-dioxa-1,7-diaza-cyclopenta[a]naphthalene (intermediate compound 16).

Example A.4

Preparation of Intermediate Compound 29

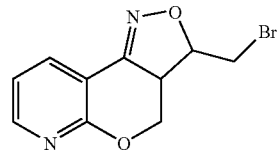

a) 2-Bromopyridine-3-carboxaldehyde (9.6 g, 0.052 mol) was treated under the reaction conditions described in Example A.2c. Yielding: 5.91 g (56%) of 2-Bromo-pyridine-3-carbaldehyde oxime (intermediate compound 17).

b) To a solution of intermediate compound 17 (5.91 g, 0.0294 mol) and pyridine (catalytic amount) in 100 ml of $CHCl_3$, N-chlorosuccinimide (4.32 g, 0.032 mol) was added portionwise at room temperature. The reaction was heated to reflux temperature for 30 min. After cooling to 0° C., dimethyl fumarate (4.24 g, 0.0294 mol) and triethylamine (4.91 ml, 0.035 mol) were added. The reaction was stirred for 48 h at room temperature. Then a saturated aqueous solution of $NaCO_3$ was added and the organic layer was separated, dried ($Na_2SO_4$), filtered and the solvent was evaporated. The residue was purified by short open column chromatography over silica gel (eluent: DCM/Ethyl acetate 95/5). The desired fractions were collected and the solvent evaporated. Yielding: 9.14 g (90%) of 3-(2-bromo-pyridin-3-yl)-4,5-dihydro-isoxazole-4,5-dicarboxylic acid dimethyl ester (intermediate compound 18).

c) To a solution of intermediate compound 18 (9.14 g, 0.027 mol) in 130 ml of tetrahydrofuran and 16 ml of ethanol, sodium borohydride (2.51 g, 0.066 mol) was added portionwise at 0° C. The reaction was stirred at this temperature for 90 min. Then a saturated solution of ammonium chloride was added. The mixture was extracted with ethyl acetate and n-BuOH. The combined organic solutions were dried ($Na_2SO_4$), filtered and the solvent was evaporated. The residue was purified by short open column chromatography over silica gel (eluent: Ethyl acetate, Ethyl acetate/MeOH saturated with ammonia 85/15). The desired fractions were collected and the solvent evaporated. Yielding: 6.8 g, (88%) of [3-(2-bromo-pyridin-3-yl)-5-hydroxymethyl-4,5-dihydro-isoxazol4-yl]-methanol (intermediate compound 19).

d) A mixture of intermediate compound 19 (6.8 g, 0.0236 mol), $K_2CO_3$ (7.2 g, 0.052 mol) and 18-crown-6 (1,4,7,10,13,16-hexaoxa-cyclooctadecane) (catalytic amount) in methylisobutyl ketone was heated to reflux overnight. Then water was added and the organic layer was separated, dried ($Na_2SO_4$), filtered and the solvent was evaporated. The residue was purified by short open column chromatography over silica gel (eluent: Ethyl acetate, Ethyl acetate/MeOH saturated with ammonia 97.5/2.5, 95/5 and 9/1). The desired fractions were collected and the solvent evaporated. Yielding: 0.48 g (10%) of (3a,4-dihydro-3H-2,5-dioxa-1,6-diaza-cyclopenta[a]naphthalen-3-yl)-methanol (intermediate compound 20).

e) Intermediate compound 20 (0.46 g, 0.00223 mol) was treated under the reaction conditions described in Example A.3. Yielding: 0.120 g (37%) of 3-bromomethyl-3a,4-dihydro-3H-2,5-dioxa-1,6-diaza-cyclopenta[a]naphthalene (intermediate compound 21).

Example A.5

Preparation of Intermediate Compound 29

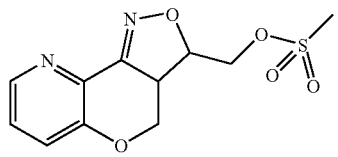

a) To a solution of 2-hydroxymethyl-3-hydroxypyridine hydrochloride (10 g, 0.062 mol) in 100 ml of DMF, imidazole (8.44 g, 0.124 mol) was added at room temperature. The solution was stirred for 30min at room temperature. Then tert-buthyldiphenylsilyl chloride (32 ml, 0.124 mol) was added dropwise at room temperature. The reaction was stirred overnight at room temperature, then the solvent was evaporated, the residue was taken up in DCM and washed with water. The organic layer was separated, dried ($Na_2SO_4$), filtered and the solvent was evaporated. The residue was purified by short open column chromatography over silica gel (eluent: Heptane/Ethyl acetate 1/1). The desired fractions were collected and the solvent evaporated. Yielding: 12.3 g (54%) of 2-(tert-butyl-diphenyl-silanyloxymethyl)-pyridin-3-ol (intermediate compound 22).

b) To a mixture of intermediate compound 22 (12.3 g, 0.034 mol) and $K_2CO_3$ (9.4 g, 0.068 mol) in DMF, 4-bromo-2-butenoic acid ethyl ester (9.36 ml, 0.068 mol) was added dropwise at 0° C., then the reaction was stirred overnight at room temperature. The solvent was evaporated, the residue was taken up in DCM and washed with water. The organic layer was separated, dried ($Na_2SO_4$), filtered and the solvent was evaporated. The residue was purified by short open column chromatography over silica gel (eluent: Heptane/Ethyl acetate 1/1). The desired fractions were collected and the solvent evaporated. Yielding: 8.72 g (54%) of 4-[2-(tert-butyl-diphenyl-silanyloxymethyl)-pyridin-3-yloxy]-but-2-enoic acid ethyl ester (intermediate compound 23).

c) To a solution of pyridine (5 ml) in 6 ml of tetrahydrofuran, pyridinium fluoride (2.5 ml) was added dropwise at 0° C. under nitrogen atmosphere and the mixture was stirred at that temperature for 15 min. Then a solution of intermediate compound 23 (8.72 g, 0.018 mol) in 16 ml of tetahydrofurane was added at 0° C. The reaction was stirred at that temperature for 2 h, then neutralized by addition of a saturated aqueous solution of $NaHCO_3$ (pH=6). The resulting mixture was extracted with DCM, the organic layer was separated, dried ($Na_2SO_4$), filtered and the solvent was evaporated. Yielding: 7.54 g (100%, crude product) of 4-(2-hydroxymethyl-pyridin-3-yloxy)-but-2-enoic acid ethyl ester (intermediate compound 24).

d) To a solution of intermediate compound 24 (7.5 g, 0.032 mol) in 150 ml of DCM, $MnO_2$ (27.8 g, 0.32 mol) was added at room temperature. The reaction was stirred overnight at room temperature, then the solid was filtered off through CELITE pad. The filtrate solvent was evaporated and the residue was purified by short open column chromatography over silica gel (eluent: Heptane/Ethyl acetate 1/1 and 1/4). The desired fractions were collected and the solvent evaporated. Yielding: 1.066 g (39%) of 4-(2-formyl-pyridin-3-yloxy)-but-2-enoic acid ethyl ester (intermediate compound 25). e) Intermediate compound 25 (1.066 g, 0.0045 mol) was treated under the reaction conditions described in Example A.1d. Yielding: 0.99 g (88%) of 4-[2-(hydroxyimino-methyl)-pyridin-3-yloxy]-but-2-enoic acid ethyl ester (intermediate compound 26).

f) To a solution of intermediate compound 26 (0.99 g, 0.00395 mol) and pyridine (catalytic amount), N-chlorosuccinimide (0.581 g, 0.00435 mol) was added portionwise at room temperature and the reaction was heated to reflux for 30 min. Then the reaction was cooled to room temperature and triethylamine was added (0.66 ml, 0.00474 mol). The reaction was stirred for 2 h at room temperature, then washed with a saturated aqueous solution of $NaHCO_3$. The organic layer was separated, dried ($Na_2SO_4$), filtered and the solvent was evaporated. Yielding: 0.98 g (100%, crude product) of 3a,4-dihydro-3H-2,5-dioxa-1,9-diaza-cyclopenta[a]naphthalene-3-carboxylic acid ethyl ester (intermediate compound 27).

g) Intermediate compound 27 (0.98 g, 0.0041 mol) was treated under the conditions described in Example A.1f. Yielding: 0.64 g (76%) of (3a,4-dihydro-3H-2,5-dioxa-1,9-diaza-cyclopenta[a]naphthalen-3-yl)-methanol (intermediate compound 28).

h) Intermediate compound 28 (0.64 g, 0.0031 mol) was treated under the conditions described in Example A.2 h. Yielding: 0.702 mg (80%) of methanesulfonic acid 3a,4- dihydro-3H-2,5-dioxa-1,9-diaza-cyclopenta[a]naphthalen-3-ylmethyl ester (intermediate compound 29).

Example A.6

Preparation of Intermediate Compound 36

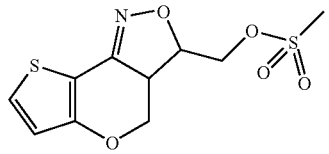

a) To a solution of 3-methoxythiophene (4.46 ml, 0.043 mol) in 60 ml of ThF, 18.92 ml (0.047 mol) of a 2.5M solution of butyllithium in tetrahydrofuran were added dropwise at room temperature under nitrogen atmosphere. The reaction was heated to reflux for 2 h, then cooled to −10° C. and DMF (4.31 ml, 0.056 mol) was added dropwise. The resulting reaction mixture was stirred at room temperature overnight. Then a 10% aqueous solution of ammonium chloride was added and the mixture was extracted with ethyl ether. The organic layer was separated, dried (Na$_2$SO$_4$), filtered and the solvent was evaporated. The residue was purified by short open column chromatography over silica gel (eluent: DCM). The desired fractions were collected and the solvent evaporated. Yielding: 4.51 g (73%) of 3-methoxy-thiophene-2-carbaldehyde (intermediate compound 30).

b) To a solution of intermediate compound 30 (4.51 g, 0.0316 mol) in 215 ml of DCM, 3.3 ml (0.0345 mol) of BBr$_3$ were added at 0° C. under nitrogen atmosphere. The reaction was stirred overnight at room temperature. The reaction was cooled to 0° C. and additional 0.52 ml (0.0055 mol) of BBr$_3$ were added. The reaction was stirred overnight at room temperature, then treated with some drops of MeOH and with a saturated aqueous solution of ammonium chloride. The mixture was filtrated through CELITE and the filtrate organic layer was separated, dried (Na$_2$SO$_4$), filtered and the solvent was evaporated. The residue was purified by short open column chromatography over silica gel (eluent: DCM/Ethyl acetate 96/4). The desired fractions were collected and the solvent evaporated. Yielding: 2.91 g (71%) of 3-hydroxy-thiophene-2-carbaldehyde (intermediate compound 31).

c) Intermediate compound 31 (2.92 g, 0.0219 mol) was treated under the conditions described in Example A.1c. Yielding: 5,74 g (95%) of 4-(2-formyl-thiophen-3-yloxy)-but-2-enoic acid ethyl ester (intermediate compound 32).

d) Intermediate compound 32 (4.87 g, 0.0197 mol) was treated under the conditions described in Example A.1d. Yielding: 5.78 g (100%, crude product) of 4-[2-(hydroxy-imino-methyl)-thiophen-3-yloxy]-but-2-enoic acid ethyl ester (intermediate compound 33).

e) Intermediate compound 33 (5.03 g, 0.0194 mol) was treated under the conditions described in Example A.1e. Yielding: 1.61 g (27%) of 3a,4-dihydro-3H-2,5-dioxa-8-thia-1-aza-as-indacene-3-carboxylic acid ethyl ester (intermediate compound 34).

f) Intermediate compound 34 (1.4 g, 0.0055 mol) was treated under the conditions described in Example A.1f.

Yielding: 1.02 g (87%) of (3a,4-dihydro-3H-2,5-dioxa-8-thia-1-aza-as-indacen-3-yl)-methanol (intermediate compound 35).

g) Intermediate compound 35 (1.17 g, 0.0055 mol) was treated under the conditions described in Example A.2 h. Yielding: 1.56 g (97%) of methanesulfonic acid 3a,4-dihydro-3H-2,5-dioxa-8-thia-1-aza-as-indacen-3-ylmethyl ester (intermediate compound 36).

B. Preparation of the Final Compounds

Example B.1

Preparation of Final Compound 1

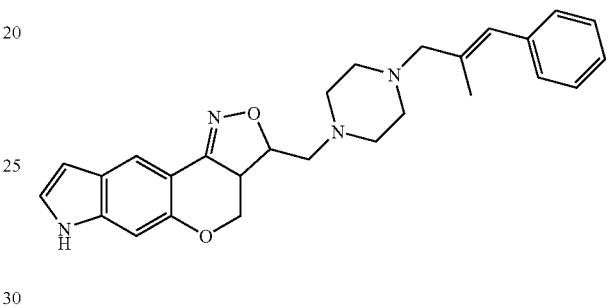

A mixture of intermediate compound 7 (prepared according to example A.1) (2.12 g, 0.0066 mol) (E) 1-(2-methyl-3-phenyl-2-propenyl)piperazine (2.16 g, 0.010 mol) KI (1.1 g, 0.0066 mol) and K$_2$CO$_3$ (0.91 g, 0.0066 mol) in methylisobutylketone (50 ml) was stirred and refluxed overnight. Then water was added and the mixture was extracted with DCM. The organic solution was separated, dried (MgSO$_4$), filtered and the solvent was evaporated. The residue was purified by short open column chromatography over silica gel (eluent: DCM/2-propanone 4/1 and 1/1). The desired fractions were collected and the solvent evaporated. The residue was washed with diisopropylether and the solid was collected. Yielding: 2.3 g (79%) of 3-[4-(2-Methyl-3-phenyl-allyl)-piperazin-1-ylmethyl]-3a,4-dihydro-3H-2,5-dioxa-1,7-diaza-dicyclopenta[a,g]naphthalene (final compound 1).

Example B.2

Preparation of Final Compound 7

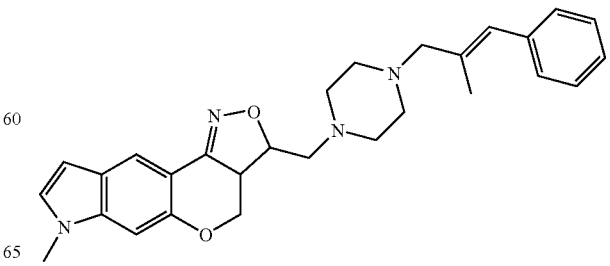

To a mixture of compound 1 (100 mg, 0.23 mmol), Na₂CO₃ (30 mg, 0.28 mmol), KOH powered (16 mg, 0.28 mmol) in 2 ml of acetonitrile and 2 ml of THF; methyliodide (17.4 μl, 0.28 mmol) was added portionwise at 0° C. The reaction was stirred at room temperature overnight. Then a 10% aqueous solution of ammonium chloride was added and the mixture was extracted with DCM. The organic solution was separated, dried (MgSO₄), filtered and the solvent was evaporated. The residue was purified by short open column chromatography over silica gel (eluent: DCM/MeOH 98/2). The desired fractions were collected and the solvent evaporated. The residue was washed with diisopropylether and the solid was collected. Yielding: 51.2 mg (49%) of 7-methyl-3-[4-(2-methyl-3-phenyl-allyl)-piperazin-1-ylmethyl]-3a,4-dihydro-3H,7H-2,5-dioxa-1,7-diaza-dicyclopenta[a,g]naphthlene (final compound 7).

Example B.3

Preparation of Final Compound 10

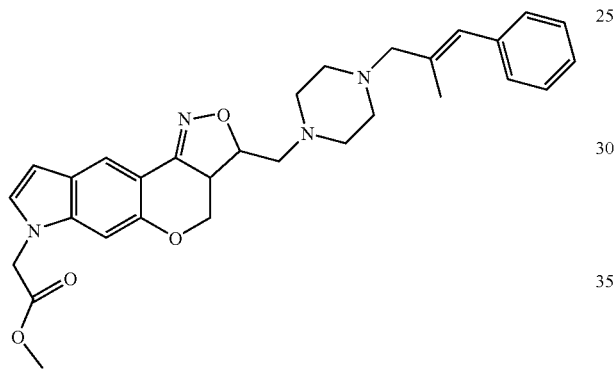

Final compound 1 (100 mg, 0.23 mmol) was treated with methyl bromoacetate (26.5 μl, 0.28 mmol) under the conditions described in Example B.2. Yielding: 39.0 mg (33%) of {3-[4-(2-methyl-3-phenyl-allyl)-piperazin-1-ylmethyl]-3a,4-dihydro-3H-2,5-dioxa- 1,7-diaza-dicyclopenta[a,g]naphthlen-7-yl}-acetic acid methyl ester (final compound 10).

Example B.4

Preparation of Final Compound 8

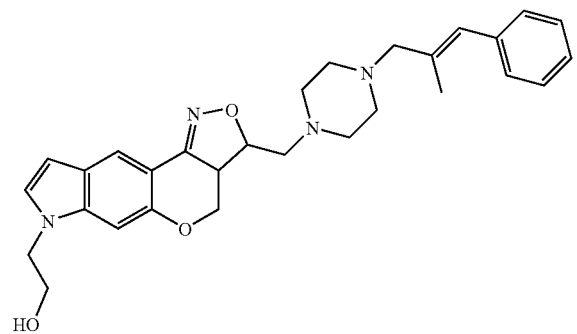

To a solution of final compound 10 (0.24 g, 4.5 mmol) in 5 ml of tetrahydrofuran and 1 ml of MeOH, sodium borohydride (42.7 mg, 1.13 mmol) was added portionwise at 0° C. The reaction was stirred for 2 h at room temperature. Then a 10% aqueous solution of ammonium chloride was added and the mixture was extracted with DCM. The organic solution was separated, dried (MgSO4), filtered and the solvent was evaporated. The residue was purified by short open column chromatography over silica gel (eluent: DCM/MeOH 98/2 and 95/5). The desired fractions were collected and the solvent evaporated. The residue was washed with diisopropylether and the solid was collected. Yielding: 87 mg (40%) of 2-{3-[4-(2-methyl-3-phenyl-allyl)-piperazin-1-ylmethyl]-3a,4-dihydro-3H-2,5-dioxa-1,7-diaza-dicyclopenta[a,g]naphthalen7-yl}ethanol (final compound 8).

Example B.5

Preparation of Final Compound 11

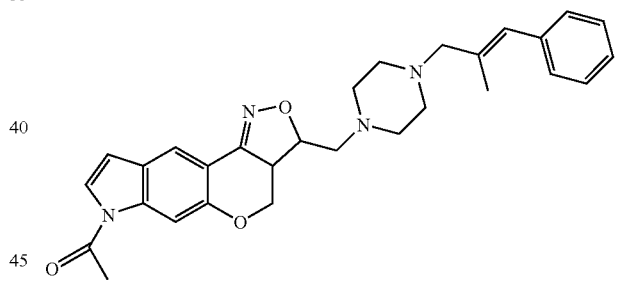

To a mixture of final compound 1 (100 mg, 0.23 mmol) and polymer supported BEMP (2-tert-butylimino-2-diethylamino-1,3-dimethylperhydro-1,3,2-diaza-phosphorine, loading 2.2 mmol/g) (0.26 g, 0.58 mmol) in 2 ml of DCM, acetyl chloride (40 μl, 0.56 mmol) was added. The reaction was stirred for 1 h at room temperature. Then the solid was filtered of through a CELITE pad and the filtrate solvent was evaporated. The residue was purified by short open column chromatography over silica gel (eluent: DCM/2-propanone 4/1). The desired fractions were collected and the solvent evaporated. The residue was washed with diisopropylether and the solid was collected. Yielding: 58.4 mg (52%) of 1-{3-[4-(2-methyl-3-phenyl-allyl)-piperazin-1-ylmethyl]-3a,4-dihydro-3H-2,5-dioxa-1,7-diaza-dicyclopenta[a,g]naphthalen7-yl}-ethanone (final compound 11).

Example B.6

Preparation of Final Compounds 16 and 17

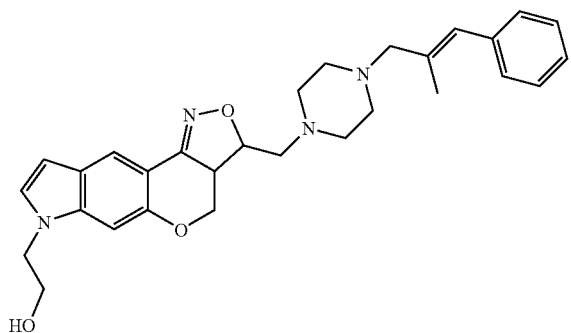

Final compound 8 (prepared according to B.4) (0.8 g, 0.00164 mol) was purified by high-performance liquid chromatography over Chiralcel OJ (eluent: hexane/MeOH/EtOH 20/24/56). The desired fractions were collected and the solvent was evaporated. Yield: fractions A and B.

Fraction A: 256 mg (32%) of A-2-{3-[4-(2-methyl-3-phenyl-allyl)-piperazin-1-ylmethyl]-3a,4-dihydro-3H-2,5-dioxa-1,7-diaza-dicyclopenta[a,g]naphthalen7-yl}-ethanol (final compound 16).

Fraction B: 276 mg (35%) of B-2-{3-[4-(2-methyl-3-phenyl-allyl)-piperazin-1-ylmethyl]-3a,4-dihydro-3H-2,5-dioxa-1,7-diaza-dicyclopenta[a,g]naphthalen7-yl}-ethanol (final compound 17).

Example B.7

Preparation of Final Compound 18

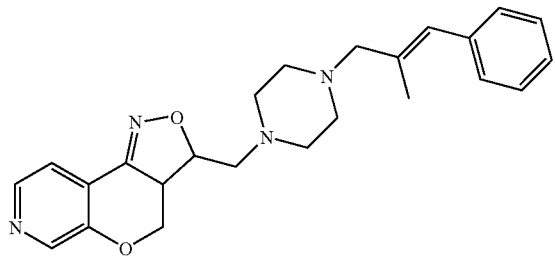

A mixture of intermediate compound 16 (prepared according to example A.3) (015 g, 0.56 mmol) and (E) 1-(2-methyl-3-phenyl-2-propenyl)piperazine (0.242 g, 1.12 mmol) in 1 ml of 1,4-dioxane was heated at 100° C. for 1 h. The mixture was taken up in DCM and washed with water. The organic solution was separated, dried (MgSO₄), filtered and the solvent was evaporated. The residue was purified by short open column chromatography over silica gel (eluent: DCM/Ethyl acetate 1/1, 1/2 and pure Ethyl acetate). The desired fractions were collected and the solvent evaporated. The residue was converted into its etanodioic acid salt in EtOH and the solid was collected. Yielding: 76 mg (27%) of 3-[4-(2-methyl-3-phenyl-allyl)-piperazin-1-ylmethyl]-3a,4-dihydro-3H-2,5-dioxa-1,7-diaza-cyclopenta[a]naphthalene oxalate salt (1/1) (final compound 18).

Example B.8

Preparation of Final Compound 19

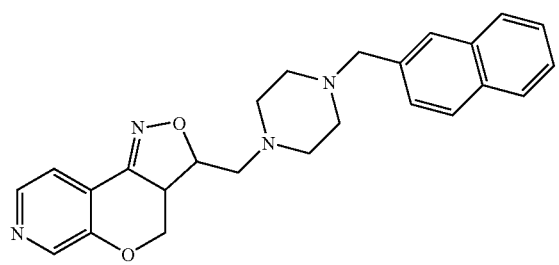

Intermediate compound 15 (prepared according to example A.2) (72 mg, 0.253 mmol) was treated with 1-Naphthalen-2-ylmethyl-piperazine (63 mg, 0.278 mmol) under the conditions described in Example B.1. The product was converted into its ethanodioic acid salt in EtOH. The solvent was evaporated and the residue was washed with acetonitrile/diisopropyl ether. The solid was collected. Yielding: 11 mg (8%) of 3-(4-naphthalen-2-ylmethyl-piperazin-1-ylmethyl)-3a,4-dihydro-3H-2,5-dioxa-1,7-diaza-cyclopenta[a]naphthalene oxalate salt (1/1) (final compound 19).

Example B.9

Preparation of Final Compound 22

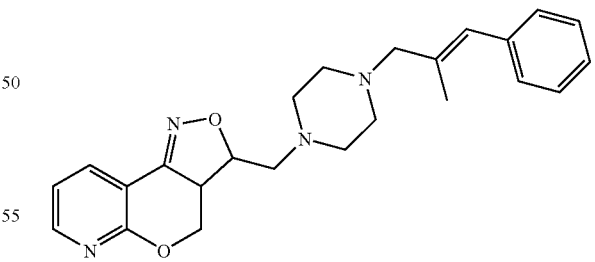

Intermediate compound 21 (prepared according to example A.4) (120 mg, 0.446 mmol) and (E) 1-(2-methyl-3-phenyl-2-propenyl)piperazine (192 mg, 0.892 mmol) in 1 ml of 1,4-dioxane was treated under the conditions described in Example B.7. Yielding: 34 mg (15%) of 3-[4-(2-methyl-3-phenyl-allyl)-piperazin-1-ylmethyl]-3a,4-dihydro-3H-2,5-dioxa-1,6-diaza-cyclopenta[a]naphthalene oxalate salt (final compound 22).

Example B.10

Preparation of Final Compound 24

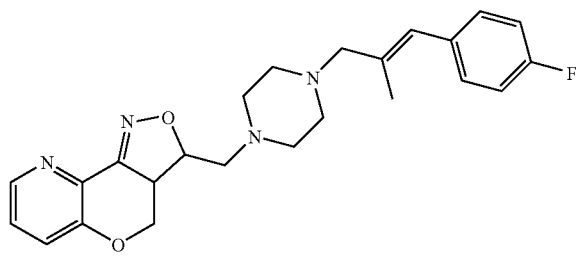

A mixture of intermediate compound 29 (prepared according to example A.5) (200 mg, 0.703 mmol), 1-[3-(4-Fluoro-phenyl)-2-methyl-allyl]-piperazine (198 mg, 0.844 mmol) and $K_2CO_3$ (117 g, 0.844 mmol) in methylisobutylketone (5 ml) was stirred and refluxed overnight. Then water was added and the mixture was extracted with DCM. The organic solution was separated, dried ($MgSO_4$), filtered and the solvent was evaporated. The residue was purified by short open column chromatography over silica gel (eluent: Heptane/Ethyl acetate 3/7, 2/8 and Ethyl acetate). The desired fractions were collected and the solvent evaporated. The residue was washed with acetonitrile/diisopropylether and the solid was collected. Yielding: 89 mg (30%) of 3-{4-[3-(4-fluoro-phenyl)-2-methyl-allyl]-piperazin-1-ylmethyl}-3a,4-dihydro-3H-2,5-dioxa-1,9-diaza-cyclopenta[a]naphthalene (final compound 24).

Example B.11

Preparation of Final Compound 27

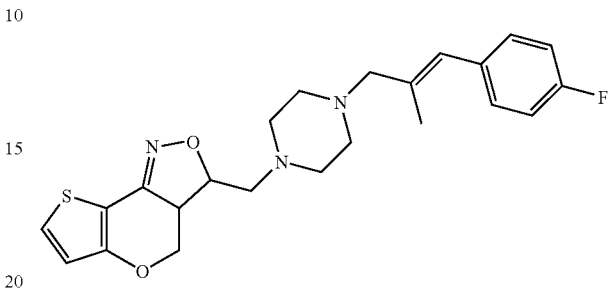

Intermediate compound 36 (prepared according to example A.6) (0.5 g, 0.0017 mol) and 1-[3-(4-Fluoro-phenyl)-2-methyl-allyl]-piperazine (0.81 g, 0.0034 mol) were treated under the conditions described in Example B.1. Yielding: 0.15 g (20%) of 3-{4-[3-(4-fluoro-pheny)-2-methyl-allyl]-piperazin-1-ylmethyl}-3a,4-dihydro-3H-2,5-dioxa-8-thia-1-aza-as-indacene (final compound 27).

The following final compounds were made accordingly:

TABLE 1

| Co. No. | Exp No. | B (R¹ group) | —R¹ | Pir—R³ | Phys.data |
|---|---|---|---|---|---|
| 1 | B.1 | indole | —H | piperazinyl-CH₂-C(CH₃)=CH-phenyl | [3α(E),3aα] |
| 2 | B.1 | indole | —H | piperazinyl-CH₂-C(CH₃)=CH-(3-F-phenyl) | [3α(E),3aα] |
| 3 | B.1 | indole | —H | piperazinyl-CH₂-C(CH₃)=CH-(4-F-phenyl) | [3α(E),3aα] |

TABLE 1-continued
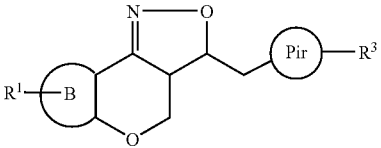
| Co. No. | Exp No. | 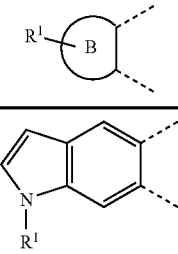 | —R¹ |  | Phys.data |
|---|---|---|---|---|---|
| 4 | B.1 | 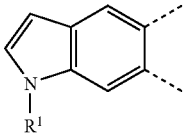 | —H |  | [3α,3aα] |
| 5 | B.1 | 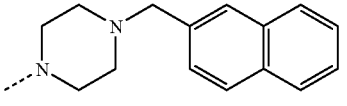 | —H | 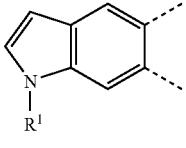 | [3α,3aα] |
| 6 | B.1 |  | —H | 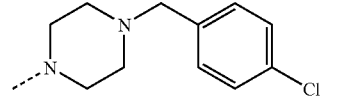 | [3α(E),3aα] |
| 7 | B.2 | 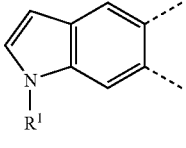 | —CH₃ |  | [3α(E),3aα] |
| 8 | B.4 | 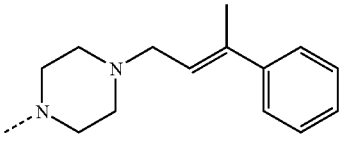 | 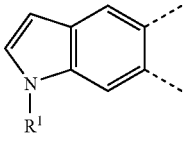 |  | [3α(E),3aα] |
| 9 | B.2 | 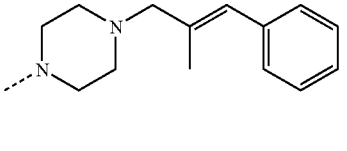 | 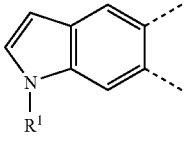 | 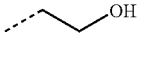 | [3α(E),3aα] |
| 10 | B.3 | 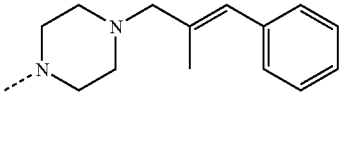 | 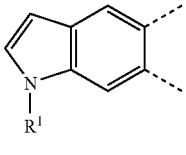 | 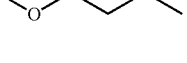 | [3α(E),3aα] |
| 11 | B.5 | 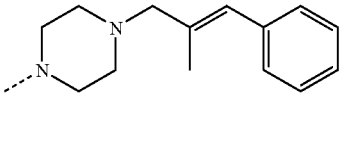 | 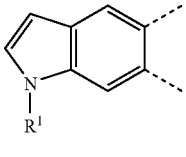 | 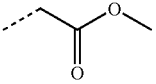 | [3α(E),3aα] |
| 12 | B.5 | 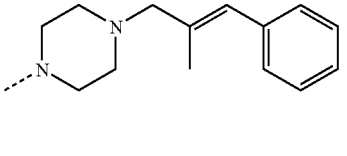 | 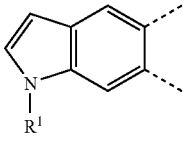 |  | [3α(E),3aα] |

TABLE 1-continued

| Co. No. | Exp No. | B (R¹ group) | —R¹ | Pir—R³ | Phys.data |
|---|---|---|---|---|---|
| 13 | B.5 | indole (N-R¹) | methyl ester (–C(=O)OCH₃) | piperazine-CH₂-C(CH₃)=CH-phenyl | [3α(E),3aα] |
| 14 | B.5 | indole (N-R¹) | –C(=O)CH₂OCH₃ | piperazine-CH₂-C(CH₃)=CH-phenyl | [3α(E),3aα] |
| 15 | B.2 | indole (N-R¹) | ethyl | piperazine-CH₂-C(CH₃)=CH-phenyl | [3α(E),3aα] |
| 16 | B.6 | indole (N-R¹) | –CH₂CH₂OH | piperazine-CH₂-C(CH₃)=CH-phenyl | A-[3α(E),3aα] |
| 17 | B.6 | indole (N-R¹) | –CH₂CH₂OH | piperazine-CH₂-C(CH₃)=CH-phenyl | B-[3α(E),3aα] |
| 18 | B.7 | pyridine | — | piperazine-CH₂-C(CH₃)=CH-phenyl | [3α(E),3aα] C₂H₂O₄ (1:1) |
| 19 | B.8 | pyridine | — | piperazine-CH₂-naphthyl | [3α,3aα] C₂H₂O₄ (1:1) |
| 20 | B.8 | pyridine | — | piperazine-CH₂-C(CH₃)=CH-(3-F-phenyl) | [3α(E),3aα] |
| 21 | B.7 | pyridine | — | piperazine-CH₂-C(CH₃)=CH-(4-F-phenyl) | [3α(E),3aα] C₂H₂O₄ (1:1) |
| 22 | B.9 | pyridine | — | piperazine-CH₂-C(CH₃)=CH-phenyl | [3α(E),3aα] C₂H₂O₄ (1:1) |

TABLE 1-continued

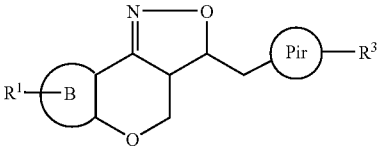

| Co. No. | Exp No. | 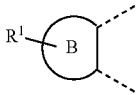 —R¹ | 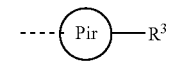 | Phys.data |
|---|---|---|---|---|
| 23 | B.10 | 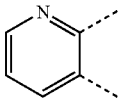 | 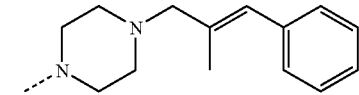 | [3α(E),3aα] $C_2H_2O_4$ (1:2) |
| 24 | B.10 | 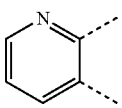 | 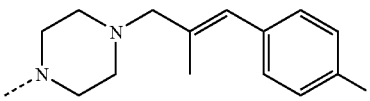 | [3α(E),3aα] |
| 25 | B.10 | 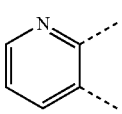 | 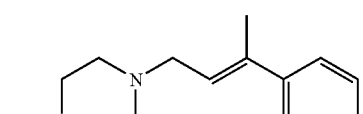 | [3α(E),3aα] |
| 26 | B.10 | 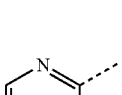 | 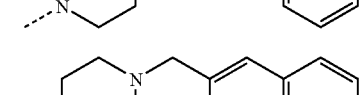 | [3α,3aα] |
| 27 | B.11 | 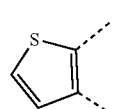 | 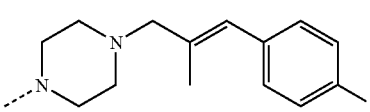 | [3α(E),3aα] |

For a selection of compounds, melting points were obtained with a Büchi melting point apparatus B-545. The heating medium is a metal block. The melting of the sample is visually observed by a magnifying lense and a big light contrast. Melting points are measured with a temperature gradient of 3 degrees Celsius/minute. The results are summarized in Table 1b.

TABLE 1b

Melting points

| Co. No. | Melting point (° C.) | Visual observation |
|---|---|---|
| 1 | 173.2-179.1 | At 173.2° C. shrink, at 177.1° C. red foam crystals, at 179.1° C. red liquid |
| 2 | 169.8-184.3 | At 169.8° C. shrink, at 181.5° C. red foam crystals, at 184.3 red liquid |
| 3 | 158.9-170.1 | At 158.9° C. shrink, at 170.1° C. red brown liquid |
| 4 | 176.6-207.3 | At 176.6° C. shrink, at 207.3° C. red sticky product |
| 5 | 131.1-154.6 | At 131.1° C. shrink, at 154.6° C. brown liquid |
| 6 | 91.6-99.2 | At 91.6° C. shrink, at 99.2° C. colourless liquid and orange sticky |
| 12 | 107.5-114.2 | At 107.5° C. shrink, at 114.2° C. yellow liquid |
| 16 | 167.9-170.2 | At 167.9° C. shrink, at 170.2° C. light yellow liquid |
| 17 | 167.5-170.5 | At 167.5° C. shrink, at 170.5° C. yellow liquid |

TABLE 1b-continued

Melting points

| Co. No. | Melting point (° C.) | Visual observation |
|---|---|---|
| 18 | 216.8-220.5 | At 216.8° C. shrink, at 218.4° C. black foam crystals, at 220.5° C. black liquid |
| 20 | 128.1-136.8 | At 128.1° C. shrink, at 136.8° C. light yellow liquid |
| 24 | 145.6-152.3 | At 145.6° C. shrink, at 152.3° C. black liquid |
| 25 | 128.1-131.1 | At 128.1° C. shrink, at 131.1° C. light yellow liquid |
| 26 | 152.4-158.1 | At 152.4° C. shrink, at 158.4° C. light yellow liquid |
| 27 | 142.3-146.0 | At 142.3° C. shrink, at 146.0° C. colourless liquid |

C. Pharmacological Examples

Example C1

Binding Experiment for $\alpha_2$-adrenergic Receptor Subtypes and for 5-HT Transporter General The interaction of the compounds of Formula (I) with h$\alpha_2$-receptors and h5-HT-transporters was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the non-bound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand. The radioligand used for $h\alpha_{2A}$, $h\alpha_{2B}$ and $h\alpha_{2C}$ receptor binding was [$^3$H]-raulwolscine and for the h5-HT transporter was [$^3$H]paroxetine.

Cell Culture and Membrane Preparation.

CHO cells, stabile transfected with human adrenergic-$\alpha_{2A}$-, -$\alpha_{2B}$ or $\alpha_{2C}$ receptor cDNA, were cultured in Dulbecco's Modified Eagle's Medium (DMEM)/Nutrient mixture Ham's F12 (ratio 1:1)(Gibco, Gent-Belgium) supplemented with 10% heat inactivated fetal calf serum (Life Technologies, Merelbeke-Belgium) and antibiotics (100 IU/ml penicillin G, 100 µg/ml streptomycin sulphate, 110 µg/ml pyruvic acid and 100 µg/ml L-glutamine). One day before collection, cells were induced with 5 mM sodiumbutyrate. Upon 80-90% of confluence, cells were scraped in phosphate buffered saline without $Ca^{2+}$ and $Mg^{2+}$ and collected by centrifugation at 1500×g for 10 min. The cells were homogenised in Tris-HCl 50 mM using an Ultraturrax homogenizer and centrifuged for 10 min at 23,500×g. The pellet was washed once by resuspension and rehomogenization and the final pellet was resuspended in Tris-HCl, divided in 1 ml aliquots and stored at −70° C.

Binding Experiment for $\alpha_2$-adrenergic Receptor Subtypes

Membranes were thawed and re-homogenized in incubation buffer (glycylglycine 25 mM, pH 8.0). In a total volume of 500 µl, 2-10 µg protein was incubated with [$^3$H]raulwolscine (NET-722) (New England Nuclear, USA) (1 nM final concentration) with or without competitor for 60 min at 25° C. followed by rapid filtration over GF/B filter using a Filtermate196 harvester (Packard, Meriden, Conn.). Filters were rinsed extensively with ice-cold rinsing buffer (Tris-HCl 50 mM pH 7.4). Filter-bound radioactivity was determined by scintillation counting in a Topcount (Packard, Meriden, Conn.) and results were expressed as counts per minute (cpm). Non-specific binding was determined in the presence of 1 µM oxymetazoline for $h\alpha_{2A}$- and $h\alpha_{2B}$ receptors and 1 µM spiroxatrine for $h\alpha_{2C}$ receptors.

Binding Experiment for 5-HT Transporter

Human platelet membranes (Oceanix Biosciences Corporation, Hanover, Md., USA) were thawed, diluted in buffer (Tris-HCl 50 mM, 120 mM NaCl and 5 mM KCl) and quickly (max 3 s) homogenised with an Ultraturrax homogenizer. In a total volume of 250 µL, 50-100 µg protein was incubated with [$^3$H]paroxetine (NET-869) (New England Nuclear, USA) (0.5 nM final concentration) with or without competitor for 60 min at 25 ° C. Incubation was stopped by rapid filtration of the incubation mixture over GF/B filters, prewetted with 0.1% polyethyleneamine, using a Filtermate196 harvester (Packard, Meriden, Conn.). Filters were rinsed extensively with ice-cold buffer and radioactivity on the filters was counted in a Topcount liquid scintillation counter (Packard, Meriden, Conn.). Data were expressed as cpm. Imipramine (at 1 µM final concentration) was used to determine the non-specific binding.

Data Analysis and Results

Data from assays in the presence of compound were calculated as a percentage of total binding measured in the absence of test compound. Inhibition curves, plotting percent of total binding versus the log value of the concentration of the test compound, were automatically generated, and sigmoidal inhibition curves were fitted using non-linear regression. The $pIC_{50}$ values of test compounds were derived from individual curves.

All compounds according to Formula (I) produced an inhibition at least at the $h\alpha_{2A}$ site (but often also at the $h\alpha_{2B}$ and $h\alpha_{2C}$ sites) and simultaneously at the 5-HT transporter site of more than 50% ($pIC_{50}$) at a test concentration ranging between $10^{-6}$ M and $10^{-9}$ M in a concentration-dependent manner.

TABLE 2

Pharmacological data.

| Co. No | $h\alpha_{2A}$ | $h\alpha_{2B}$ | $h\alpha_{2C}$ | 5-HTT |
|---|---|---|---|---|
| 20 | 9.2 | — | 8.8 | 7.6 |
| 18 | 8.9 | — | 8.8 | 6.7 |
| 23 | 8.9 | — | 8.4 | 6.7 |
| 18 | 8.8 | 8.8 | 8.8 | 7.5 |
| 27 | 8.7 | — | 8.1 | 7.1 |
| 25 | 8.7 | — | 7.8 | 6.2 |
| 11 | 8.6 | — | 9.0 | 8.2 |
| 14 | 8.5 | — | 8.9 | 8.4 |
| 7 | 8.5 | — | 9.1 | 8.3 |
| 13 | 8.4 | — | 8.4 | 7.9 |
| 1 | 8.3 | 8.4 | 9.0 | 8.4 |
| 24 | 8.2 | — | 7.5 | 6.7 |
| 21 | 8.2 | — | 7.8 | 7.1 |
| 12 | 8.2 | — | 8.5 | 7.7 |
| 26 | 8.1 | — | 7.3 | 7.4 |
| 6 | 8.1 | — | 8.6 | 8.3 |
| 2 | 8.1 | 8.3 | 9.0 | 8.3 |
| 9 | 8.1 | 8.1 | 9.1 | 8.7 |
| 19 | 8.0 | — | 7.4 | 7.0 |
| 17 | 8.0 | 8.3 | 8.7 | 6.3 |
| 10 | 7.9 | 8.3 | 9.1 | 8.7 |
| 15 | 7.9 | 8.4 | 8.6 | 8.3 |
| 3 | 7.8 | 7.6 | 8.7 | 8.2 |
| 8 | 7.8 | 8.3 | 8.7 | 8.4 |
| 4 | 7.6 | 7.3 | 8.4 | 8.8 |
| 5 | 6.7 | — | 7.4 | 7.8 |
| 16 | 6.5 | 7.7 | 7.3 | 6.3 |
| 22 | 6.2 | — | 7.1 | 5.2 |

The invention claimed is:

1. A compound according to the general Formula (I)

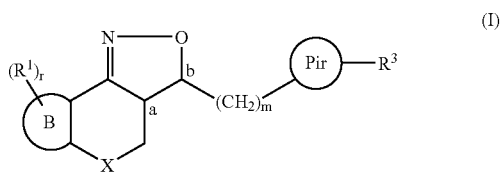

the pharmaceutically acceptable acid or base addition salts thereof, the stereochemically isomeric forms thereof, or the N-oxide forms thereof, wherein:

X is CH$_2$, N—R$^7$, S or O;

R$^7$ is selected from the group consisting of hydrogen, alkyl, Ar, Ar-alkyl, alkylcarbonyl, alkyloxycarbonyl and mono- and dialkylaminocarbonyl;

B is a radical, optionally substituted with r radicals R', according to anyone of Formula (B-a) or (B-b) and fused to the isoxazolinyl moiety by either of the bond pairs (c,d), (d,e) or (e,f)

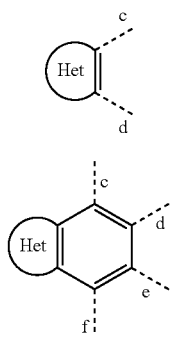

wherein
- Het is an optionally substituted 5- or 6-membered heterocyclic ring, selected from the group consisting of pyridinyl, pyrazinyl, pyrimidinyl, pyridazinyl, furanyl, thienyl, pyrrolyl, oxazolyl, thiazolyl, imidazolyl, pyrazolyl, isothiazolyl, isoxazolyl, oxadiazolyl and triazolyl;
- each R$^1$ is, independently from each other, selected from the group consisting of hydrogen, hydroxy, amino, nitro, cyano, halo and alkyl and, only when R' is attached to a N-atom, is further selected from the group of alkyloxyalkyl, alkyloxyalkyloxyalkyl, alkyloxycarbonylalkyl, fonnyl, alkylcarbonyl, alkyloxycarbonyl, alkyloxyalkylcarbonyl and mono- and dialkylaminocarbonyl;
- r is an integer ranging from 0 to 6;
- a and b are asymmetric centers;
- (CH$_2$)$_m$ is a straight hydrocarbon chain of m carbon atoms, m being an integer ranging from 1 to 4;
- Pir is a radical according to any one of Formula (IIa), (IIb) or (IIc)

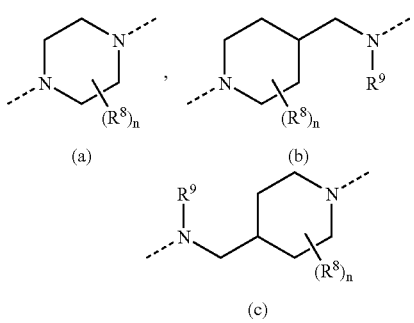

optionally substituted with n radicals R$^8$, wherein:
- each R$^8$ is independently from each other, selected from the group consisting of hydroxy, amino, nitro, cyano, halo and alkyl;
- n is an integer ranging from 0 to 5;
- R$^9$ is selected from the group consisting of hydrogen, alkyl and formyl;

R$^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

Ar is phenyl or naphthyl, optionally substituted with one or more halo, cyano, oxo, hydroxy, alkyl, formyl, alkyloxy or amino radicals; and alkyl represents a straight or branched saturated hydrocarbon radical having from 1 to 6 carbon atoms or a cyclic saturated hydrocarbon radical having from 3 to 6 carbon atoms, optionally substituted with one or more halo, cyano, oxo, hydroxy, formyl or amino radicals.

2. The compound according to claim 1, wherein R$^3$ is a radical according to any one of Formula (IIIa), (IIIb) or (IIIc)

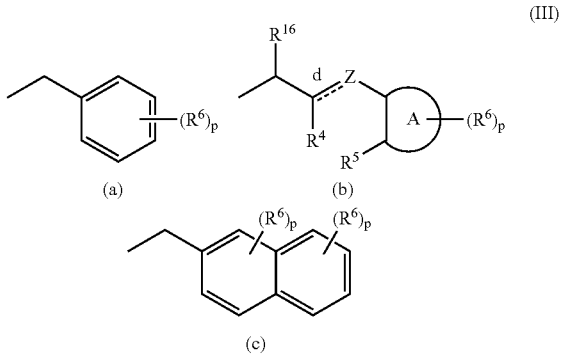

wherein:
- d is a single bond while Z is a bivalent radical selected from the group consisting of —CH$_2$—, —C(=O)—, —CH(OH)—, —C(=N—OH)—, —CH(alkyl)—, —O—, —S—, —S(=O)—, —NH— and —SH—; or d is a double bond while Z is a trivalent radical of formula =CH— or =C(alkyl)—;
- A is a 5- or 6-membered aromatic homocyclic or heterocyclic ring, selected from the group consisting of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;
- P is an integer ranging from 0 to 6;
- R$^4$ and R$^5$ are each, independently from each other, selected from the group consisting of hydrogen, alkyl, Ar, biphenyl, halo and cyano ; or
- R$^4$ and R$^5$ may be taken together to form a bivalent radical —R$^4$—R$^5$— selected from the group consisting of —CH$_2$—, =CH—, —CH$_2$—CH$_2$—, —CH=CH—, —O—, —NH—, =N—, —S—, —CH$_2$N(-alkyl)—, —N(-alkyl)CH$_2$—, —CH$_2$NH—, —NHCH$_2$—, —CH=N—, —N=CH—, —CH$_2$O— and —OCH$_2$—;
- each R$^6$ is independently from each other, selected from the group consisting of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or
- two vicinal radicals R$^6$ may be taken together to form a bivalent radical —R$^6$—R$^6$— selected from the group consisting of —CH$_2$—CH$_2$—O—, —O—CH$_2$—

—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$— and R$^{16}$ is selected from the group consisting of hydrogen, alkyl, Ar and Ar-alkyl.

3. A compound according to claim 2, wherein X=O; m=1; B is a radical according to Formula (B-a) or (B-b), Pir is a radical according to Formula (IIa) wherein n=0 ; R$^3$ is a radical according to according to any one of Formula (IIIa), (IIIb) or (IIIc) wherein d is a double bond while Z is a trivalent radical of formula =CH— or =C(alkyl)—; A is a phenyl ring; R$^4$ is hydrogen or alkyl ; R$^5$ and R$^{16}$ are hydrogen; R$^6$ is hydrogen or halo and p=1.

4. A compound according to claim 1, wherein Het is selected from the group consisting of pyridinyl, thienyl and pyrrolyl, each radical optionally substituted on a N atom with a radical selected from the group consisting of hydrogen, alkyl, hydroxyalkyl, alkyloxyalkyloxyalkyl, alkyloxycarbonylalkyl, alkylcarbonyl, alkyloxycarbonyl and alkyloxyalkylcarbonyl.

5. A method of treating a warm-blooded animal suffering from depression, anxiety, movement disorders, psychosis, Parkinson's disease, or body weight disorders comprising administering a compound according to claim 1 to said animal.

6. A pharmaceutical composition comprising a pharmaceutically acceptable carrier and, as active ingredient, a therapeutically effective amount of a compound according to claim 1.

7. A process for making a pharmaceutical composition comprising mixing a compound according to claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 7,501,418 B2 | Page 1 of 1 |
| APPLICATION NO. | : 10/524123 | |
| DATED | : March 10, 2009 | |
| INVENTOR(S) | : José Ignacio Andrés-Gil et al. | |

It is certified that error appears in the above-identified patent and that said Letters Patent is hereby corrected as shown below:

On the Title Page,
Item (75) Inventors:
Line 8, delete "Hendrikus Megens," and insert -- Hendrikus Petrus Megens, --.

Item (30) Foreign Application Priority Data:
After "02078373" insert -- .4 --.

After Item (57) ABSTRACT, delete "7 Claims," and insert -- 6 Claims, --.

Column 4,
Line 21, delete "allcyloxyalkyl," and insert -- alkyloxyalkyl, --.

Column 22,
Line 4, delete "naphthalene-3-methanol" and insert -- naphthalene-3-yl)-methanol --.

Column 26,
Line 38, a new paragraph should begin with "e) Intermediate compound 25...".

Column 28,
Line 47, delete "ylmethyl]-3a,4-dihydro-3H-2,5-dioxa" and insert
-- ylmethyl]-3a,4-dihydro-3H,7H-2,5-dioxa --.

Column 45,
Line 14, delete "according to" (second occurrence).
Line 17, after "are" insert -- each --.

Column 46,
Claim 5, lines 6-10, should be deleted.

Signed and Sealed this
Fifteenth Day of November, 2011

David J. Kappos
*Director of the United States Patent and Trademark Office*